(12) United States Patent
Kura et al.

(10) Patent No.: US 7,556,843 B2
(45) Date of Patent: Jul. 7, 2009

(54) PHOTOSENSITIVE RESIN COMPOSITION

(75) Inventors: Hisatoshi Kura, Takarazuka (JP); Hidetaka Oka, Takarazuka (JP); Masaki Ohwa, Kobe (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 88 days.

(21) Appl. No.: 11/818,073

(22) Filed: Jun. 13, 2007

(65) Prior Publication Data

US 2007/0259278 A1  Nov. 8, 2007

Related U.S. Application Data

(62) Division of application No. 10/484,357, filed as application No. PCT/EP02/07989 on Jul. 18, 2002, now Pat. No. 7,247,659.

(30) Foreign Application Priority Data

Jul. 26, 2001 (EP) ................... 01810734

(51) Int. Cl.
*G03F 7/00* (2006.01)
*C08J 3/28* (2006.01)

(52) U.S. Cl. ............ 427/500; 427/504; 427/510; 427/514; 430/7; 430/286.1; 430/321; 522/8; 522/12; 522/16; 522/39; 522/121

(58) Field of Classification Search .......... 430/7, 430/286.1, 321; 427/500, 504, 510, 514; 522/8, 39, 12, 16, 121

See application file for complete search history.

(56) References Cited

U.S. PATENT DOCUMENTS

| | | | | |
|---|---|---|---|---|
| 5,077,402 A | 12/1991 | Desobry et al. | ........ | 544/87 |
| 5,362,603 A | 11/1994 | Katoh et al. | ........ | 430/281.1 |
| 6,114,092 A | 9/2000 | Miyagawa et al. | ........ | 430/285.1 |
| 6,251,548 B1 | 6/2001 | Sega et al. | ........ | 430/7 |
| 6,733,935 B2 | 5/2004 | Kishimoto et al. | ........ | 430/7 |
| 6,806,028 B2 | 10/2004 | Kubota | ........ | 430/270.1 |
| 6,824,858 B2 | 11/2004 | Iwaida et al. | ........ | 428/209 |
| 6,841,587 B2 | 1/2005 | Yamamoto | ........ | 522/39 |
| 6,844,130 B2 | 1/2005 | Nishikubo et al. | ........ | 430/258 |
| 2002/0015901 A1* | 2/2002 | Takebe et al. | ........ | 430/7 |
| 2002/0022186 A1* | 2/2002 | Takebe | ........ | 430/7 |
| 2003/0215746 A1* | 11/2003 | Kohiyama et al. | ........ | 430/280.1 |
| 2004/0191671 A1 | 9/2004 | Hsu | ........ | 430/270.1 |
| 2004/0265730 A1 | 12/2004 | Takahashi et al. | ........ | 430/270.1 |

FOREIGN PATENT DOCUMENTS

WO   98/00759   1/1998

OTHER PUBLICATIONS

Derwent Abstract 1992-245718 for JP 04164901 (1992).
Derwent Abstract 2001-061115 [07] for WO 00/68740.
Derwent Abstract 2000-045318/04 for JP 11306964 (1999).
Derwent Abstract 1999-381501 for JP 11149862 (1999).
Derwent Abstract 99-249656/21 for JP 11072909 (1999).
Derwent Abstract 99-236642/20 for JP 11065102 (1999).

* cited by examiner

*Primary Examiner*—Susan W Berman
(74) *Attorney, Agent, or Firm*—Joseph C. Suhadolnik

(57) ABSTRACT

A photopolymerization process for producing pigmented and non-pigmented articles comprises irradiating with electromagnetic radiation in the range from 190 to 600 nm, or with electron beam or with X-rays a photosensitive composition which can be developed by alkali solution which composition comprises (A) a polymer containing at least one carboxylic acid group in the molecule and having a molecular weight of 200,000 or less,
(B) selected α-aminoalkylphenone compounds as photoinitiators and
(C) an ester of a polyol, wherein the polyol is partially or fully esterified with an ethylenically unsaturated carboxylic acid a monomeric, oligomeric or polymeric compound having at least one olefinic double bond.

15 Claims, No Drawings

PHOTOSENSITIVE RESIN COMPOSITION

This application is a divisional of U.S. application Ser. No. 10/484,357 now U.S. Pat. No. 7,247,659 filed Jan. 20, 2004 as Application No. PCT/EP02/07989 on Jul. 18, 2002, which application is hereby incorporated by reference.

From U.S. Pat. No. 5,077,402 it is known that α-aminoalkylphenones are photoinitiators. In JP 2678684 B2 color filter resist compositions comprising 2-benzyl-2-dimethylamino-1-(4-morpholinophenyl)butan-1-one as photoinitiator are disclosed. In WO 98/00759 A1 and WO 0068740 A1 alkali developable solder resist compositions comprising the photoinitiator are disclosed. Similar alkali developable compositions for manufacturing plasma display panels are disclosed in JP 11306964 A2, JP 11149862 A2, JP 11072909 A2, and JP 11065102 A2.

In photopolymerization technology there still exists a need for compositions suitable in particular as imaging formulations which are highly reactive, alkali developable, easy to handle, exhibit good developability and meet the high requirements of the industry regarding properties like, for example, thermal stability and storage stability.

Surprisingly it was found that photosensitive compositions comprising, (A) an oligomer or polymer containing at least one carboxylic acid group in the molecule and having a molecular weight of 200,000 or less;
(B) at least one photoinitiator compound of formula I

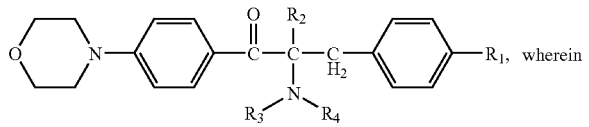

(I), wherein $R_1$ is linear or branched $C_1$-$C_{12}$alkyl;
$R_2$ is linear or branched $C_1$-$C_4$alkyl;
$R_3$ and $R_4$ independently of one another are linear or branched $C_1$-$C_8$alkyl; and
(C) a monomeric, oligomeric or polymeric compound having at least one olefinic double bond, exhibit an unexpectedly good performance.

Component (A) in the composition according to the invention is an oligomer or polymer, which contains at least one free carboxylic acid group in the molecule and which has a molecular weight of 200,000 or less than 200,000.

Examples for suitable components (A) are polymers having a molecular weight of about 2,000 to 200,000, preferably 2,000 to 150,000, 2,000 to 100,000 or 5,000 to 100,000 (binders). Examples of alkali developable binders are acrylic polymers having a carboxylic acid function as a pendant group, such as conventionally known copolymers obtained by copolymerizing an ethylenic unsaturated carboxylic acid such as (meth)acrylic acid, 2-carboxyethyl (meth)acrylic acid, 2-carboxypropyl(meth)acrylic acid, itaconic acid, crotonic acid, maleic acid, maleic acid monomethyl ester, maleic acid monoethyl ester, maleic acid monopropyl ester, maleic acid monobutyl ester, maleic acid monobenzyl ester, maleic acid mono(2-ethylhexyl)ester, maleic acid monohydroxyethyl ester, maleic acid monohydroxypropyl, fumaric acid, fumaric acid monomethyl ester, fumaric acid monoethyl ester, fumaric acid monopropyl ester, fumaric acid monobutyl ester, fumaric acid monobenzyl ester, fumaric acid mono(2-ethylhexyl)ester, fumaric acid monohydroxyethyl ester, fumaric acid monohydroxypropyl, and ω-carboxypolycaprolactone mono(meth)acrylate with one or more monomers selected from esters of (meth)acrylic acid, such as methyl(meth)acrylate, ethyl (meth)acrylate, propyl(meth)acrylate, butyl(meth) acrylate, benzyl(meth)acrylate, 2-ethylhexyl(meth)acrylate, hydroxyethyl(meth)acrylate, hydroxypropyl(meth)acrylate, glycerol mono(meth)acrylate, tricyclo[5.2.1.0$^{2,6}$]decan-8-yl (meth)acrylate, glycidyl(meth)acrylate, 2-methylglycidyl (meth)acrylate, 3,4-epoxybutyl(meth)acrylate, and 6,7-epoxyheptyl(meth)acrylate; esters of maleic acid and fumaric acid, such as maleic acid dimethyl ester, maleic acid diethyl ester, maleic acid dipropyl ester, maleic acid dibutyl ester, maleic acid dibenzyl ester, maleic acid di(2-ethylhexyl)ester, maleic acid dihydroxyethyl ester, maleic acid dihydroxypropyl, fumaric acid dimethyl ester, fumaric acid diethyl ester, fumaric acid dipropyl ester, fumaric acid dibutyl ester, fumaric acid dibenzyl ester, fumaric acid di(2-ethylhexyl) ester, fumaric acid dihydroxyethyl ester, and fumaric acid dihydroxypropyl; vinyl aromatic compounds, such as styrene, α-methylstyrene, vinyltoluene, p-chlorostyrene, vinyl benzyl glycidyl ether; amide type unsaturated compounds, (meth)acrylamide, diacetone acrylamide, N-methylolacrylamide, N-butoxymethacrylamide; and polyolefin type compounds, such as butadiene, isoprene, chloroprene and the like, mono-2-[(meth)acryloyloxy]ethyl succinate, N-phenylmaleimide, maleic anhydride; methacrylonitrile, methyl isopropenyl ketone, vinyl acetate, vinyl propionate, vinyl pivalate, polystyrene macromonomer, or polymethyl(meth)acrylate macromonomer. Examples of copolymers are copolymers of acrylates and methacrylates with acrylic acid or methacrylic acid and with styrene or substituted styrene, phenolic resins, for example novolak, (poly)hydroxystyrene, and copolymers of hydroxystyrene with alkyl acrylates, acrylic acid and/or methacrylic acid. Preferred examples of copolymers are copolymers of methyl methacrylate/methacrylic acid, copolymers of benzyl methacrylate/methacrylic acid, copolymers of methyl methacrylate/ethyl acrylate/methacrylic acid, copolymers of benzyl methacrylate/methacrylic acid/styrene, copolymers of benzyl methacrylate/methacrylic acid/hydroxyethyl methacrylate, copolymers of methyl methacrylate/butyl methacrylate/methacrylic acid/styrene, copolymers of methyl methacrylate/benzyl methacrylate/methacrylic acid/hydroxyphenyl methacrylate, copolymers of methacrylic acid/styrene/benzyl methacrylate/glycerol monomethacrylate/N-phenylmaleimide, copolymers of methacrylic acid/ω-carboxypolycaprolactone monoacrylate/styrene/benzyl/methacrylate/glycerol monomethacrylate/N-phenylmaleimide.

The polyimide binder resin in the present invention can be a polyimide precursor, for example a poly(amic acid ester) compound, optionally having photopolymerizable side groups either attached to the backbone or to the ester groups in the molecule, or it can be, for example, a poly(amic acid) to which preferably an acrylate or methacrylate having at least one basic group in its molecule is added in solution, for example an aminoacrylate or aminomethacrylate.

Further examples for component (A) are oligomers or polymers obtained by reaction of a saturated or unsaturated polybasic acid anhydride with a product of the reaction of an epoxy compound and an unsaturated monocarboxylic acid. As epoxy compounds which are employed for the preparation the most interesting ones are novolak type epoxies and bisphenol type epoxies.

The aforementioned resin curable by an activated energy ray is obtained by causing a reaction product of a novolak type epoxy compound (as described afterward) and an unsaturated monocarboxylic acid to react with a dibasic acid anhydride such as phthalic anhydride or an aromatic polycarboxylic acid anhydride such as trimellitic acid anhydride or pyromellitic acid anhydride. In this case, the resin proves particularly suitable when, in the production thereof, the amount of the aforementioned acid anhydride used for the reaction exceeds 0.15 mol per each of the hydroxyl groups possessed by the reaction product of the novolak type epoxy compound and the unsaturated carboxylic acid.

The acid value (the acid value is expressed by milligram number of potassium hydroxide necessary for neutralizing 1 gram of resin) of the resin so obtained suitably falls in the range of 45 to 160 mg KOH/g, preferably 50 to 140 mg KOH/g.

When the number of ethylenically unsaturated bonds present in the molecular unit of the resin curable by the activated energy ray is small, the photosetting proceeds slowly and it is desirable to use a novolak type epoxy compound as a raw material.

The novolak type epoxy compounds are represented by phenol novolak type epoxy resins and cresol novolak type epoxy resins. Compounds as are produced by causing epichlorohydrin to react with a pertinent novolak resin by the conventional method can be used.

The aforementioned resin is also produced by a reaction of a polycarboxylic acid anhydride such as benzophenone tetracarboxylic acid dianhydride, pyromellitic acid dianhydride, trimellic acid anhydride and/or a dibasic acid anhydride with a reaction product of a bisphenol epoxy compound such as bisphenol fluorene epoxy resin or bisphenol A epoxy resin and an unsaturated monocarboxylic acid. Typical examples of the photopolymerizable bisphenol type compounds are described in JP 6-1938-A, JP 7-64281-A, JP 9-241339-A, JP 9-304929 and JP 10-301276. For the purpose of lowering the viscosity of the ink, it is possible to use bisphenol A type epoxy compounds.

Typical examples of the aforementioned acid anhydride are dibasic acid anhydrides such as for example maleic anhydride, succinic anhydride, itaconic anhydride, phthalic anhydride, tetrahydrophthalic anhydride, hexahydrophthalic anhydride, methylhexahydrophthalic anhydride, endomethylenetetrahydrophthalic anhydride, methyl-endomethylenetetrahydrophthalic anhydride, chlorendic anhydride, and methyltetrahydrophthalic anhydride; aromatic polycarboxylic anhydrides such as for example trimellitic anhydride, pyromellic anhydride, and benzophenone-tetracarboxylic dianhydride, biphenyltetracarboxylic acid dianhydride, diphenyl ether tetracarboxylic acid dianhydride, diphenylsulfonetetracarboxylic acid dianhydride, hexafluoroisopropylidenediphthalic anhydride: and polycarboxylic anhydride derivatives such as 5-(2,5-dioxotetrahydrofuryl)-3-methyl-3-cyclohexene-1,2-dicarboxylic anhydride.

Further examples for component (A) are reaction products obtained by adding epoxy group containing acrylic acid ester or methacrylic acid ester compounds to a part of the carboxyl groups of a copolymer resulting of the reaction of acrylate or methacrylate with acrylic acid or methacrylic acid.

The copolymer of acrylic acid ester and/or methacrylic acid ester and acrylic acid and/or methacrylic acid is obtained by copolymerizing one, two or more acrylic acid esters and/or methacrylic acids. Suitable esters are represented by formula (1)

$R_a$ is a hydrogen atom or a methyl group,
$R_b$ is an aliphatic hydrocarbon group having 1 to 6 carbon atoms, and suitable acrylic acids and/or methacrylic acids are represented by formula (2);

wherein $R_a$ has the same meaning as given above.

The copolymerization is carried out according to routine methods such as for example solution polymerization.

Preferably the molar ratio between the acrylic acid ester and/or methacrylic acid ester and the acrylic acid and/or methacrylic acid is from 30:70 to 70:30.

The ester group of each of the acrylic acid esters and/or methacrylic acid esters may be appropriately selected from various aliphatic groups containing 1 to 6 carbon atoms.

The reaction product is obtained by adding to the copolymer thus obtained acrylic acid ester and/or methacrylic acid ester having a terminal epoxy group, represented by the following formula (3);

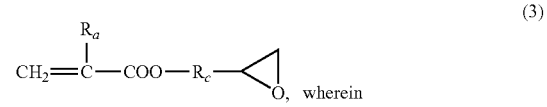

$R_a$ has the same meaning as described above;
$R_c$ is an aliphatic hydrocarbon group or aromatic hydrocarbon group having 1 to 12 carbon atoms.

In order to obtain a reaction product suitable for the present invention, a compound of formula (3) is added to the aforementioned monomers of formula (1) and (2) at a ratio of 10 to 40 mol %, to provide the copolymer with ultraviolet curability.

The reaction product thus obtained preferably has an average molecular weight in the range of 20,000 to 70,000; the softening point suitably is in the range from 35° C. to 130° C., and the acid value is 50 to 150.

Further examples for component (A) are resins having α,β-unsaturated double bonds on the side chains, and having an acid value of 50-200. The photopolymerizable resin, for example, is constituted of 70-95% by weight of an ethylenically unsaturated acid component and a copolymerizable component thereof. It is an addition product formed between a carboxyl group-containing resin having an acid value of no less than 500, preferably no less than 600 and in particular no less than 620, and having a number average molecular weight of 1,000-100,000, preferably 3,000-70,000, and an unsaturated compound having an α,β-unsaturated double bond and an epoxy group. The content of the ethylenically unsaturated acid component in the carboxyl group-containing resin of the photopolymerizable resin is 70-95% by weight, due to which the photopolymerizable resin (A) does not become insoluble in water or dilute alkali aqueous solution even after an unsaturated compound having an α,β-unsaturated double bond and an epoxy group is added thereto, and retains its solubility. Examples of such resins are described in JP 8-339081-A.

The carboxyl group-containing resin (A), for example, is produced by dissolving 70-95% by weight, preferably 78-88% by weight and in particular 80-85% by weight, of an ethylenically unsaturated acid monomer and 5-30% by weight, preferably 22-12% by weight and in particular 15-20% by weight, of a copolymerizable monomer in a suitable unreactive solvent and thermally polymerizing the solution at 45-120° C. in the presence of a thermal polymerization initiator. Thus, a carboxyl group-containing resin having an acid value of no less than 500 and a number average molecular weight of 1,000-100,000 can be produced in a high safety and a high stability.

Specific examples of the ethylenically unsaturated monomer suitable for production of the carboxyl group-containing resin (A) include acrylic acid, methacrylic acid, crotonic acid, isocrotonic acid, angelic acid, tiglic acid, 2-ethylacrylic acid, 3-propylacrylic acid, 3-isopropylacrylic acid, succinic acid mono-hydroxyethylacrylate, phthalic acid mono-hydroxyethylacrylate, dihydrophthalic acid mono-hydroxyethylacrylate, tetrahydrophthalic acid mono-hydroxyethylacrylate, hexahydrophthalic acid monohydroxyethyl-acrylate, acrylic acid dimer, acrylic acid trimer, ω-carboxy-polycaprolactone monoacrylate and ω-carboxy-polycaprolactone monomethacrylate. Among these monomers, preferred are acrylic acid, methacrylic acid, crotonic acid, isocrotonic acid, angelic acid, tiglic acid, 2-ethylacrylic acid, 3-propylacrylic acid, 3-isopropylacrylic acid, ω-carboxy-polycaprolactone monoacrylate, ω-carboxy-polycaprolactone monomethacrylate, and the like; and particularly preferred are acrylic acid, methacrylic acid, crotonic acid, isocrotonic acid, angelic acid, tiglic acid, 2-ethylacrylic acid, 3-propylacrylic acid, 3-isopropylacrylic acid, ω-carboxy-polycaprolactone monoacrylate, and ω-carboxy-polycaprolactone monomethacrylate. These monomers may be used either alone or in mixtures of two or more.

Suitable copolymerizable monomers are acrylic esters, methacrylic esters, vinyl monomers, styrene type monomers and cyclic ester monomers. Specific examples thereof include 2-hydroxymethyl acrylate, 2-hydroxymethyl methacrylate, 2-hydroxyethyl acrylate, 2-hydroxyethyl methacrylate, 2-hydroxypropyl acrylate, 2-hydroxypropyl methacrylate, ethyleneglycol monomethyl ether acrylate, ethyleneglycol monomethyl ether methacrylate, ethyleneglycol monoethyl ether acrylate, ethyleneglycol monoethyl ether methacrylate, glycerol acrylate, glycefol methacrylate, dipentaerythritol pentamethacrylate, dipentaerythritol pentaacrylate, dimethylamino-ethyl acrylate, dimethylamino-ethyl methacrylate, tetrahydrofurfuryl acrylate, tetrahydro-furfuryl methacrylate, acrylic acid amide, methacrylic acid amide, acrylonitrile, methacrylonitrile, methyl acrylate, methyl methacrylate, ethyl acrylate, ethyl methacrylate, butyl acrylate, butyl methacrylate, isobutyl acrylate, isobutyl methacrylate, 2-ethylhexyl acrylate, 2-ethylhexyl-methacrylate, benzyl acrylate, benzyl methacrylate, acrylic acid carbitol, methacrylic acid carbitol, ε-caprolactone-modified tetrafurfuryl acrylate, ε-caprolactone-modified tetrafurfuryl methacrylate, diethyleneglycol ethoxyl acrylate, isodecyl acrylate, isodecyl methacrylate, octyl acrylate, octyl methacrylate, lauryl acrylate, lauryl methacrylate, tridecyl acrylate, tridecyl methacrylate, stearyl acrylate, stearyl methacrylate and the like. These monomers may be used either alone or in mixtures of two or more.

Suitable thermal polymerization initiators are for example, 2,2'-azobis-(2,4-dimethylvaleronitrile) (usable temperature 45-70° C.), 2,2'-azobis(isobutyronitrile) (usable temperature 60-90° C.), 2,2'-azobis(2-methylisobutyronitrile) (usable temperature 60-95° C.), tert-butyl peroctoate (usable temperature 75-100° C.), 1,1'-azobis(cyclohexane-1-carbonitrile) (usable temperature 80-110° C.) or 1-[(1-diazo-1-methylethyl)azo]-formamide (usable temperature 95-120° C.). In general, for example, at least one of the cited compounds is used.

The carboxyl group-containing resin produced according to the aforementioned method is then modified into a photopolymerizable resin whose carboxyl group is esterified and whose side chains have α,β-unsaturated double bonds, through an esterification with an unsaturated compound having an α,β-unsaturated double bond and an epoxy group. Examples of suitable compounds having an α,β-unsaturated double bond and an epoxy group, are given below. For example, at least one member selected from the group consisting of glycidyl acrylate, glycidyl methacrylate, compounds of the formula 4, 5, 6, as defined below, is used.

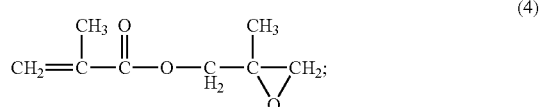
(4)

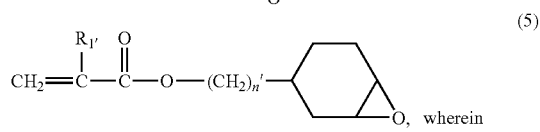
(5)

$R_1'$ is hydrogen or methyl and n' is an integer of 1-10;

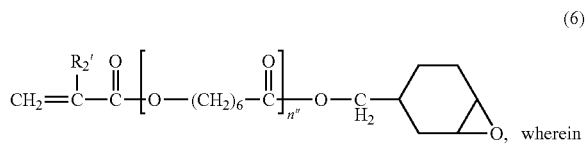
(6)

$R_2'$ is hydrogen or methyl and n" is an integer of 1-3.

Among these compounds, compounds having alicyclic epoxy groups are particularly preferred, because these compounds have a high reactivity with carboxyl group-containing resins, accordingly the reaction time can be shortened. These compounds further do not cause gelation in the process of reaction and make it possible to carry out the reaction stably. On the other hand, glycidyl acrylate and glycidyl methacrylate are advantageous from the viewpoint of sensitivity and heat resistance because they have a low molecular weight and can give a high conversion of esterification.

The photopolymerizable resin obtained by the above-mentioned method has α,β-unsaturated double bonds on its side chains. Its acid value is 50-200, preferably 70-150, and in particular 85-120. Its number average molecular weight is 7,000-10,000, and its glass transition point (hereinafter referred to as Tg) is 30-120° C. When the photopolymerizable resin is used as a solder resist, an acid value of no less than 70 is preferable, because other additive ingredients may further be added to the composition.

An inert organic solvent is used at the time of carrying out the esterification and preparing the photosensitive resin composition.

Commercially available unsaturated compounds (A), as described before are, for example EB3800, EB9692, EB9694, EB9695, EB9696 (UCB Chemicals), KAYARAD TCR1025 (Nippon Kayaku Co., LTD.), NEOPOL8319 (U-Pica), EA-6340 (Shin Nakamura Chemical Co., Ltd.), ACA200M, ACA250 (Daicel Industries, Ltd.).

Preferred is a composition, wherein the oligomer or polymer (A) is a binder polymer, in particular a copolymer of (meth)acrylate and (meth)acrylic acid, or a resin obtained by the reaction of a saturated or unsaturated polybasic acid anhydride with a product of the reaction of an epoxy compound and an unsaturated monocarboxylic acid, or is an addition product formed between a carboxyl group-containing resin and an unsaturated compound having an α,β-unsaturated double bond and an epoxy group.

The photosensitive compositions of the invention comprise at least one photoinitiator (B) of formula I as described above.

$C_1$-$C_{12}$alkyl is linear or branched and is for example $C_1$-$C_{10}$-, $C_1$-$C_8$-, $C_1$-$C_6$-, $C_1$-$C_4$-, $C_6$-$C_{10}$-, $C_8$-$C_{10}$-, $C_6$-$C_8$-, $C_4$-$C_8$- or $C_4$-$C_{10}$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl and dodecyl.

$R_1$ is for example linear or branched $C_1$-$C_4$alkyl, in particular methyl, ethyl, isopropyl, n-propyl, isobutyl and n-butyl, $R_2$ is for example methyl, ethyl or propyl, in particular ethyl and $R_3$ and $R_4$ in particular independently of one another are linear or branched $C_1$-$C_4$alkyl, in particular methyl.

Preferred compounds of formula I are

The unsaturated compounds (C) include one or more olefinic double bonds. They are for example of low (monomeric) or high (oligomeric) molecular mass. Examples of monomers containing a double bond are alkyl or hydroxyalkyl acrylates or methacrylates, for example methyl, ethyl, butyl, 2-ethylhexyl or 2-hydroxyethyl acrylate, isobornyl acrylate, methyl methacrylate or ethyl methacrylate. Silicone acrylates are also advantageous. Other examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers containing two or more double bonds are the diacrylates of ethylene glycol, propylene glycol, neopentyl glycol, hexamethylene glycol or of bisphenol A, and 4,4'-bis(2-acryloyloxyethoxy)diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris(2-acryloylethyl)isocyanurate.

Examples of polyunsaturated compounds of relatively high molecular mass (oligomers) are acrylated epoxy resins, acrylisized polyesters, polyesters containing vinyl ether or epoxy groups, and also polyurethanes and polyethers. Further examples of unsaturated oligomers are unsaturated polyester resins, which are usually prepared from maleic acid, phthalic

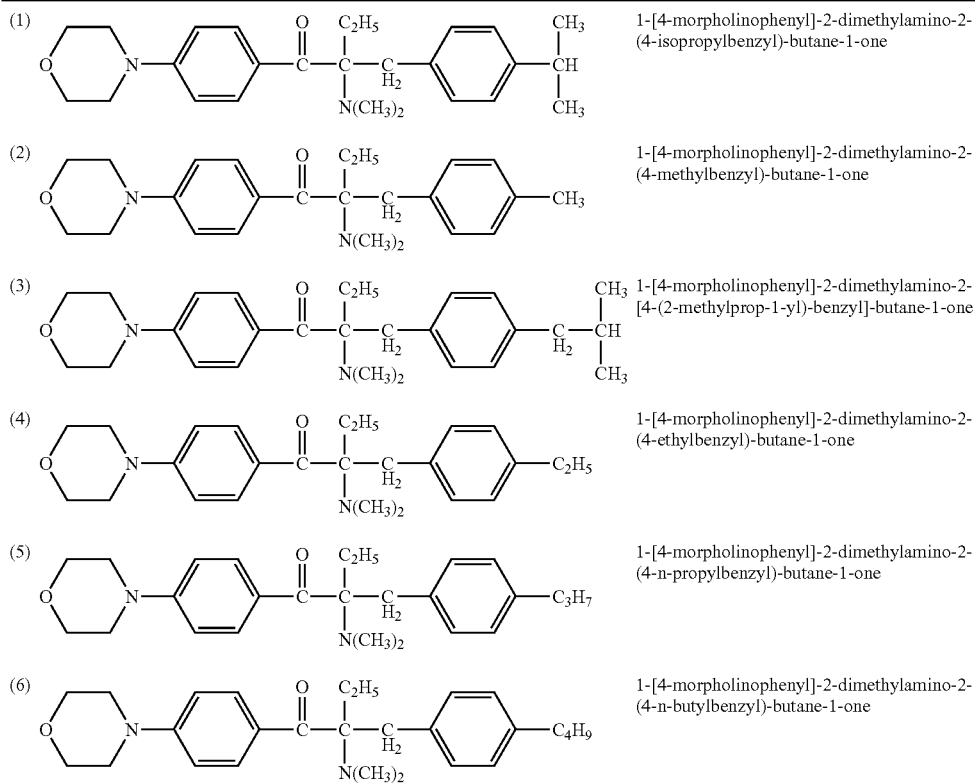

These photoinitiator compounds are known to the public. Their preparation is for example described in U.S. Pat. No. 5,077,402, col. 16 ff.

The suitable amount of the component (B) is from 0.015 to 100 parts by weight, preferably 0.03 to 80 parts by weight, based on 100 parts by weight of component (A).

acid and one or more diols and have molecular weights of from about 500 to 3000. In addition it is also possible to employ vinyl ether monomers and oligomers, and also maleate-terminated oligomers with polyester, polyurethane, polyether, polyvinyl ether and epoxy main chains. Of particular suitability are combinations of oligomers which carry vinyl ether groups and of polymers as described in WO 90/01512. However, copolymers of vinyl ether and maleic acid-functionalized monomers are also suitable. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, for example unsaturated polyesters, polyamides and polyurethanes and copolymers thereof, polymers and copolymers containing (meth)acrylic groups in side chains, and also mixtures of one or more such polymers.

Examples of unsaturated carboxylic acids are acrylic acid, methacrylic acid, crotonic acid, itaconic acid, cinnamic acid, and unsaturated fatty acids such as linolenic acid or oleic acid. Acrylic and methacrylic acid are preferred.

Suitable polyols are aromatic and, in particular, aliphatic and cycloaliphatic polyols. Examples of aromatic polyols are hydroquinone, 4,4'-dihydroxydiphenyl, 2,2-di(4-hydroxyphenyl)propane, and also novolaks and resols. Examples of polyepoxides are those based on the above-mentioned polyols, especially the aromatic polyols, and epichlorohydrin. Other suitable polyols are polymers and copolymers containing hydroxyl groups in the polymer chain or in side groups, examples being polyvinyl alcohol and copolymers thereof or polyhydroxyalkyl methacrylates or copolymers thereof. Further polyols which are suitable are oligoesters having hydroxyl end groups.

Examples of aliphatic and cycloaliphatic polyols are alkylenediols having preferably 2 to 12 C-atoms, such as ethylene glycol, 1,2- or 1,3-propanediol, 1,2-, 1,3- or 1,4-butanediol, pentanediol, hexanediol, octanediol, dodecanediol, diethylene glycol, triethylene glcyol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl) amine, trimethylolethane, trimethylolpropane, pentaerythritol, dipentaerythritol and sorbitol.

The polyols may be partially or completely esterified with one unsaturated carboxylic acid or with different unsaturated carboxylic acids, and in partial esters the free hydroxyl groups may be modified, for example etherified or esterified with other carboxylic acids.

Examples of esters are:

trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol tris-itaconate, dipenta-erythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetra methacrylate, sorbitol pentaacrylate, sorbitol hexaacrylate, oligoester acrylates and methacrylates, glycerol diacrylate and triacrylate, 1,4-cyclohexane diacrylate, bisacrylates and bismethacrylates of polyethylene glycol with a molecular weight of from 200 to 1500, or mixtures thereof.

Also suitable as components (C) are the amides of identical or different, unsaturated carboxylic acids with aromatic, cycloaliphatic and aliphatic polyamines having preferably 2 to 6, especially 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine, di(β-aminoethoxy)- or di(β-aminopropoxy)ethane. Other suitable polyamines are polymers and copolymers, preferably with additional amino groups in the side chain, and oligoamides having amino end groups. Examples of such unsaturated amides are methylenebisacrylamide, 1,6-hexamethylenebisacrylamide, diethylenetriaminetrismethacrylamide, bis (methacrylamidopropoxy)ethane, β-methacrylamidoethyl methacrylate and N[(β-hydroxyethoxy)ethyl]acrylamide.

Suitable unsaturated polyesters and polyamides are derived, for example, from maleic acid and from diols or diamines. Some of the maleic acid can be replaced by other dicarboxylic acids. They can be used together with ethylenically unsaturated comonomers, for example styrene. The polyesters and polyamides may also be derived from dicarboxylic acids and from ethylenically unsaturated diols or diamines, especially from those with relatively long chains of, for example 6 to 20 C atoms. Examples of polyurethanes are those composed of saturated or unsaturated diisocyanates and of unsaturated or, respectively, saturated diols.

Polymers with (meth)acrylate groups in the side chain are likewise known. They may, for example, be reaction products of epoxy resins based on novolaks with (meth)acrylic acid, or may be homo- or copolymers of vinyl alcohol or hydroxyalkyl derivatives thereof which are esterified with (meth) acrylic acid, or may be homo- and copolymers of (meth) acrylates which are esterified with hydroxyalkyl(meth) acrylates.

The photopolymerizable compounds (C) can be used alone or in any desired mixtures. It is preferred to use mixtures of polyol (meth)acrylates.

Preferably component (C) is a monomer with more than two acrylate or methacrylate groups.

The components (C) as described above are used singly or as a mixture of two or more than two. The suitable amount is from 5 to 200 parts by weight, preferably 10 to 150 parts by weight, based on 100 parts by weight of component (A).

Additionally, optionally an organic solvent can be added to the composition of the invention as component (D). Examples for suitable organic solvents are ketones such as ethyl methyl ketone, cyclohexanone, etc.; aromatic hydrocarbons such as toluene, xylene, tetramethylbenzene, etc.; glycol ethers such as methyl cellosolve, ethyl cellosolve, butyl cellosolve, benzyl cellosolve, phenyl cellosolve, methylcarbitol, butylcarbitol, propylene glycol monomethyl ether, dipropylene glycol monomethyl ether, dipropylene glycol monobutyl ether, triethylene glycol monoethyl ether, etc.; esters such as ethyl acetate, butyl acetate, ethyl ethoxypropionate and esterified products of the above glycol ethers such as cellosolve acetate, butyl cellosolve acetate, carbitol acetate, butyl carbitol acetate, propylene glycol monomethyl ether acetate; alcohols such as ethanol, propanol, n-butanol, n-hexanol, n-heptanol, n-octanol, ethylene glycol, propylene glycol, etc.; aliphatic hydrocarbons such as octane, decane, etc.; a petroleum type solvent such as petroleum ether, petroleum naphtha, hydrogenated petroleum naphtha, solvent naphtha, etc. and others. The organic solvent is used for diluting the resin so that it can be coated easily.

Photopolymerization can also be accelerated by adding further photosensitizers or coinitiators (as component (E)) which shift or broaden the spectral sensitivity. These are, in particular, aromatic compounds, for example benzophenone and derivatives thereof, thioxanthone and derivatives thereof, anthraquinone and derivatives thereof, coumarin and phenothiazine and derivatives thereof, and also 3-(aroylmethylene)thiazolines, rhodanine, camphorquinone, but also eosine, rhodamine, erythrosine, xanthene, thioxanthene, acridine, e.g. 9-phenylacridine, 1,7-bis(9-acridinyl)heptane, 1,5-bis(9-acridinyl)pentane, cyanine and merocyanine dyes.

Specific examples of such compounds are

1. Thioxanthones

Thioxanthone, 2-isopropylthioxanthone, 2-chlorothioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di-[2-(2-methoxyethoxy)ethoxycarbonyl]-thioxanthone, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-carboxylic acid polyethyleneglycol ester, 2-hydroxy-3-(3,4-dimethyl-9-oxo-9H-thioxanthon-2-yloxy)-N,N,N-trimethyl-1-propanaminium chloride;

2. Benzophenones benzophenone, 4-phenyl benzophenone, 4-methoxy benzophenone, 4,4'-dimethoxy benzophenone, 4,4'-dimethyl benzophenone, 4,4'-dichlorobenzophenone 4,4'-bis(dimethylamino)benzophenone, 4,4'-bis(diethylamino)benzophenone, 4-methyl benzophenone, 2,4,6-trimethylbenzophenone, 4-(4-methylthiophenyl)-benzophenone, 3,3'-dimethyl-4-methoxy benzophenone, methyl-2-benzoylbenzoate, 4-(2-hydroxyethylthio)-benzophenone, 4-(4-tolylthio)benzophenone, 4-benzoyl-N,N,N-trimethyl-benzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxamidecyl)-benzophenone, 4-benzoyl-N,N-dimethyl-N-[2-(1-oxo-2-propenyl)oxy]ethyl-benzenemethanaminium chloride;

3. Coumarins

Coumarin 1, Coumarin 2, Coumarin 6, Coumarin 7, Coumarin 30, Coumarin 102, Coumarin 106, Coumarin 138, Coumarin 152, Coumarin 153, Coumarin 307, Coumarin 314, Coumarin 314T, Coumarin 334, Coumarin 337, Coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)coumarin], 3,3'-carbonyl-bis(7-methoxycoumarin), 3,3'-carbonyl-bis(7-diethylamino-coumarin), 3-isobutyroyl-coumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylamino-coumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, 7-diethylamino-3-phenylcoumarin, the coumarin derivatives disclosed in JP 09-179299-A and JP 09-325209-A, for example 7-[{4-chloro-6-(diethylamino)-S-triazine-2-yl}amino]-3-phenylcoumarin;

4. 3-(aroylmethylene)-thiazolines 3-methyl-2-benzoylmethylene-β-naphthothiazoline, 3-methyl-2-benzoylmethylene-benzothiazoline, 3-ethyl-2-propionylmethylene-β-naphthothiazoline;

5. Rhodanines 4-dimethylaminobenzalrhodanine, 4-diethylaminobenzalrhodanine, 3-ethyl-5-(3-octyl-2-benzothiazolinylidene)-rhodanine, the rhodanine derivatives, formulae [1], [2], [7], disclosed in JP 08-305019A;

6. Other Compounds acetophenone, 3-methoxyacetophenone, 4-phenylacetophenone, benzil, 4,4'-bis(dimethylamino)benzil, 2-acetylnaphthalene, 2-naphthaldehyde, dansyl acid derivatives, 9,10-anthraquinone, anthracene, pyrene, aminopyrene, perylene, phenanthrene, phenanthrenequinone, 9-fluorenone, dibenzosuberone, curcumin, xanthone, thiomichier's ketone, α-(4-dimethylamino-benzylidene) ketones, e.g. 2,5-bis(4-diethylaminobenzylidene)cyclopentanone, 2-(4-dimethylamino-benzylidene)-indan-1-one, 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)phthalimide, phenothiazine, methylphenothiazine, amines, e.g. N-phenylglycine, ethyl 4-dimethylaminobenzoate, butoxyethyl 4-dimethylaminobenzoate, 4-dimethylaminoacetophenone, triethanolamine, methyldiethanolamine, dimethylaminoethanol, 2-(dimethylamino) ethyl benzoate, p-dimethylaminobenzoate, The action of the amines can be intensified by the addition of aromatic ketones of the benzophenone type. Examples of amines which can be used as oxygen scavengers are substituted N,N-dialkylanilines, as are described in EP 339841. Other accelerators, coinitiators and autoxidizers are thiols, thioethers, disulfides, phosphonium salts, phosphine oxides or phosphines, as described, for example, in EP 438123, in GB 2180358 and in JP Kokai Hei 6-68309.

In some cases it may be advantageous to use sensitizer compounds in combination with the compounds (B). Another object of the invention therefore resides in a composition which additionally to the components (A), (B) and (C) comprises at least one photosensitizer compound (E), in particular a compound selected from the group consisting of benzophenone and its derivatives, thioxanthone and its derivatives, anthraquinone and its derivatives, or coumarin and its derivatives.

In addition to the components (A)-(E) the photopolymerizable mixtures may include a thermosetting component (F).

Examples of component (F) are compounds having epoxy groups as thermosetting component. For example a solid or liquid known epoxy compound may be used, and said epoxy compound is used depending on required characteristics. For example, when the plating resistance is to be improved, a liquid epoxy resin is used, and when water resistance is required, an epoxy resin having a large number of methyl groups on a benzene ring or a cycloalkyl ring is employed. A preferred epoxy resin, is a bisphenol S type epoxy resin such as BPS-200 produced by Nippon Kayaku Co., Ltd., EPX-30 produced by ACR Co., Epiculon EXA-1514 produced by Dainippon Ink & Chemicals Inc., etc.; a bisphenol A type epoxy resin such as Epiculon N-3050, N-7050, N-9050 produced by Dainippon Ink & Chemicals Inc., XAC-5005, GT-7004, 6484T, 6099 produced by Asahi Kasei Epoxy Co., Ltd., etc.; a bisphenol F type epoxy resin such as YDF-2004, YDF2007 produced by Tohto Kasei Co., etc.; a diglycidyl phthalate resin such as Blemmer DGT produced by Nippon Oil and Fats Co., Ltd., etc.; a heterocyclic epoxy resin such as TEPIC produced by Nissan Chemical Industries, Ltd., Araldite PT810 produced by Asahi Kasei Epoxy Co., Ltd., etc.; a bixylenol type epoxy resin such as YX-4000 produced by Yuka Shell Co., etc.; a biphenol type epoxy resin such as YL-6056 produced by Yuka Shell Co., etc.; a tetraglycidyl xylenoylethane resin such as ZX-1063 produced by Tohto Kasei Co., etc.; a novolak type epoxy resin such as EPPN-201, EOCN-103, EOCN-1020, EOCN-1025 and BRRN produced by Nippon Kayaku Co., Ltd., ECN-278, ECN-292 and ECN-299 produced by Asahi Kasei Epoxy Co., Ltd., GY-1180, ECN-1273 and ECN-1299 produced by Asahi Kasei Epoxy Co., Ltd., YDCN-220L, YDCN-220HH, YDCN-702, YDCN-704, YDPN-601 and YDPN-602 produced by Tohto Kasei Co., Epiculon-673, N-680, N-695, N-770 and N-775 produced by Dainippon Ink & Chemicals Inc., etc.; a novolak type epoxy resin of bisphenol A such as EPX-8001, EPX-8002, EPPX-8060 and EPPX-8061 produced by Asahi Kasei Epoxy Co., Ltd., Epiculon N-880 produced by Dainippon Ink & Chemicals Inc., etc.; a chelate type epoxy resin such as EPX-49-69 and EPX-49-30 produced by Asahi Denka Kogyo K.K., etc.; a glyoxal type epoxy resin such as YDG-414 produced by Tohto Kasei Co., etc.; an amino group-containing epoxy resin such as YH-1402 and ST-110 produced by Tohto Kasei Co., YL-931 and YL-933 produced by Yuka Shell Co., etc.; a rubber-modified epoxy resin such as Epiculon TSR-601 produced by Dainippon Ink & Chemicals Inc., EPX-84-2 and EPX-4061 produced by Asahi Denka Kogyo K.K., etc.; a dicyclopentadiene phenolic type epoxy resin such as DCE-400 produced by Sanyo-Kokusaku Pulp Co., Ltd., etc.; a silicone-modified epoxy resin such as X-1359 produced by Asahi Denka Kogyo K.K., etc.; an e-caprolactone-modified epoxy resin such as Plaque G-402 and G-710 produced by Dicel Chemical Industries, Ltd., etc. and others. Further, partially esterified compounds of these epoxy compounds (e.g. esterified by (meth)acrylates) can be used in combination.

Preferably thermosetting component is a bisphenol A, bisphenol S, bisphenol F or novolak type epoxy compound.

The suitable amount of thermosetting component (F) to be used according to the present invention is 10 to 150 parts by weight, preferably 20 to 80 parts by weight, based on 100 parts by weight of component (A).

The invention therefore also pertains to a composition additionally to the components (A), (B) and (C) comprising at least one compound having epoxy groups (F).

Further, in addition to components (A), (B) and (C), as well as optional (D), (E) and (F), various additives (G), in amounts customary in the art, may be employed in the composition according to the invention.

In the photosensitive thermosetting resin composition of the present invention, for improving characteristics such as adhesion property, hardness, etc., if necessary, there may be used an inorganic filler (G1) such as for example barium sulfate, barium titanate, silicon oxide powder, particulate silicone oxide, amorphous silica, talc, clay, magnesium carbonate, calcium carbonate, aluminium oxide, aluminium hydroxide, mica powder, etc. The ratio of the filler in the formulation is 0 to 60% by weight, preferably 5 to 40% by weight of the photosensitive thermosetting resin composition.

The composition optionally additionally comprises as component (G2) epoxy curing promoters such as, for example, an amine compound, an imidazole compound, a carboxylic acid, a phenol, a quaternary ammonium salt, or a methylol group-containing compound. The amount of said curing agent to be used is in the range of 0 to 10% by weight, preferably 0.05 to 5% by weight, of the photosensitive thermosetting resin composition.

Examples of further additives (G) are thermal inhibitors, which are intended to prevent premature polymerization, examples being hydroquinone, hydroquinone derivatives, p-methoxyphenol, β-naphthol or sterically hindered phenols, such as 2,6-di-tert-butyl-p-cresol. In order to increase the stability on storage in the dark it is possible, for example, to use copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, for example tetramethylammonium chloride or trimethylbenzylammonium chloride, or hydroxylamine derivatives, for example N-diethylhydroxylamine. To exclude atmospheric oxygen during the polymerization it is possible to add paraffin or similar wax-like substances which, being of inadequate solubility in the polymer, migrate to the surface in the beginning of polymerization and form a transparent surface layer which prevents the ingress of air. It is also possible to apply an oxygen-impermeable layer. Light stabilizers which can be added in a small quantity are UV absorbers, for example those of the hydroxyphenylbenzotriazole, hydroxyphenyl-benzophenone, oxalamide or hydroxyphenyl-s-triazine type. These compounds can be used individually or in mixtures, with or without sterically hindered amines (HALS).

Examples of such UV absorbers and light stabilizers (G3) are 1. 2-(2'-hydroxyphenyl)benzotriazoles for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-diтert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotrizole, 2-(2'-hydroxy-4'-octoxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)-benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethyl-hexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-yl-phenol]; transesterification product of 2-[3'-tert-butyl-5'-(2-methoxycarbonylethyl)-2'-hydroxy-phenyl]- benzotriazole with polyethylene glycol 300; [R—CH$_2$CH$_2$—COO(CH$_2$)$_3$]$_2$— where R=3'-tert-butyl-4'-hydroxy-5'-2H-benzotriazol-2-yl-phenyl.

2. 2-Hydroxybenzophenones, for example the 4-hydroxy-, 4-methoxy-, 4-octoxy-, 4-decyloxy, 4-dodecyloxy-, 4-benzyloxy-, 4,2',4'-trihydroxy- and 2'-hydroxy-4,4'-dimethoxy derivative.

3. Esters of substituted or unsubstituted benzoicacids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, and 2-methyl-4,6-di-tert-butylphenyl 3,5-di-tert-butyl-4-hydroxybenzoate.

4. Acrylates, for example isooctyl or ethyl α-cyano-β,β-diphenyl acrylate, methyl α-carbomethoxycinnamate, butyl or methyl α-cyano-β-methyl-p-methoxycinnamate, methyl α-carboxymethoxy-p-methoxycinnamate and N-(β-carbomethoxy-β-cyanovinyl)-2-methylindoline.

5. Sterically hindered amines, for example bis-(2,2,6,6-tetramethylpiperidyl)sebacate, bis(2,2,6,6-tetramethylpiperidyl)succinate, bis-(1,2,2,6,6-pentamethylpiperidyl)sebacate, bis(1,2,2,6,6-pentamethylpiperidyl) n-butyl-3,5-di-tert-butyl-4-hydroxybenzylmalonate, condensation product of 1-hydroxyethyl-2,2,6,6-tetramethyl-4-hydroxypiperidine and succinic acid, condensation product of N,N'-bis-(2,2,6,6-tetramethyl-4-piperidyl)hexamethylenediamine and 4-tert-octylamino-2,6-dichloro-1,3,5-s-triazine, tris-(2,2,6,6-tetramethyl-4-piperidyl)nitrilotriacetate, tetrakis-(2,2,6,6-tetramethyl-4-piperidyl)-1,2,3,4-butane tetraoate, 1,1'-(1,2-ethanediyl)bis(3,3,5,5-tetramethyl-piperazinone), 4-benzoyl-2,2,6,6-tetramethylpiperidine, 4-steparyloxy-2,2,6,6-tetramethylpiperidine, bis-(1,2,2,6,6-pentamethylpiperidyl) 2-n-butyl-2-(2-hydroxy-3,5-di-tert-butylbenzyl) malonate, 3-n-octyl-7,7,9,9-tetramethyl-1,3,8-triazaspiro-[4.5]-decane-2,4-dione, bis-(1-octyloxy-2,2,6,6-tetramethylpiperidyl)sebacate, bis-(1-octyloxy-2,2,6,6-tetramethylpiperidyl)succinate, condensation product of N,N'-bis-(2,2,6,6-tetramethyl-4-piperidyl)hexamethylenediamine and 4-morpholino-2,6-dichloro-1,3,5-triazine, condensation product of 2-chloro-4,6-di-(4-n-butylamino-2,2,6,6-tetramethylpiperidyl)-1,3,5-triazine and 1,2-bis-(3-aminopropyl-amino)ethane, condensation product of 2-chloro-4,6-di-(4-n-butylamino-1,2,2,6,6-pentamethylpiperidyl)-1,3,5-triazine and 1,2-bis-(3-aminopropylamino) ethane, 8-acetyl-3-dodecyl-7,7,9,9-tetramethyl-1,3,8-triazaspiro[4,5]decane-2,4-dione, 3-dodecyl-1-(2,2,6,6-tetramethyl-4-piperidyl)pyrrolidine-2,5-dione and 3-dodecyl-1-(1,2,2,6,6-penta-methyl-4-piperidyl)-pyrrolidine-2,5-dione.

6. Oxalamides, for example 4,4'-dioctyloxyoxanilide, 2,2'-diethoxyoxanilide, 2,2'-dioctyloxy-5,5'-di-tert-butyloxanilide, 2,2'-didodecyloxy-5,5'di-tert-butyloxanilide, 2-ethoxy-2'-ethyl-oxanilide, N,N'-bis-(3-dimethylaminopropyl) oxalamide, 2-ethoxy-5-tert-butyl-2'-ethyl-oxanilide and its mixture with 2-ethoxy-2'-ethyl-5,4'-di-tert-butyloxanilide, mixtures of o- and p-methoxy- and of o- and p-ethoxy-disubstituted oxanalides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis-(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxy-phenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethylphenyl)-1,3,5-triazine, 2-[2-hydroxy-4-(2-hydroxy-3-octyloxy-propyloxy)phenyl]-4,6-bis(2,4-dimethylphenyl)-1,3,5-triazine, 2-[4-dodecyl/tridecyl-oxy-(2-hydroxypropyl)oxy-2-hydroxy-phenyl]-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythrityl diphosphite, tris-(2,4-di-tert-butylphenyl)phosphite, diisodecyl pentaerythrityl diphosphite, bis-(2,4-di-tert-butylphenyl)pentaerythrityl diphosphite, bis-(2,6-di-tert-butyl-4-methylphenyl)pentaerythrityl diphosphite, bis-isodecyloxy pentaerythrityl diphosphite, bis-(2,4-di-tert-butyl-6-methylphenyl)pentaerythrityl diphosphite, bis-(2,4,6-tri-tertbutylphenyl)pentaerythrityl diphosphite, tristearyl sorbityl triphosphite, tetrakis-(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis-(2,4-di-tert-butyl-6-methylphenyl)methyl phosphite and bis(2,4-di-tert-butyl-6-methylphenyl)ethyl phosphite.

The invention therefore also pertains to a composition additionally to the components (A), (B) and (C) comprising at least one UV-absorber or light stabilizer compound (G3).

Further, if, necessary, there may be used known additives such as a known coloring agents, e.g. Phthalocynine Blue, Phthalocyanine Green, Diazo Yellow, Crystal Violet, titanium oxide, carbone black, naphthalene black, etc.

Accordingly, subject of the invention are compositions as described above, comprising further additives (G), which are selected from the group consisting of inorganic fillers, colorants, dispersants, thermal polymerization inhibitors, thickeners, antifoaming agents and leveling agents, in particular inorganic fillers.

It is further possible to add chain transfer agents which are customary in the art to the compositions according to the invention. Examples are mercaptans, amines and benzothiazol.

The curing process can be assisted by, in particular, compositions which are pigmented (for example with titanium dioxide), by adding a component which under thermal conditions forms free radicals, for example an azo compound such as 2,2'-azobis(4-methoxy-2,4-dimethylvaleronitrile), a triazene, diazo sulfide, pentazadiene or a peroxy compound, for instance a hydroperoxide or peroxycarbonate, for example t-butyl hydroperoxide, as described for example in EP 245639.

The compositions according to the invention may comprise as further additive (G) a photoreducable dye, e.g., xanthene-, benzoxanthene-, benzothioxanthene-, thiazine-, pyronine-, porphyrine- or acridine dyes, and/or trihalogenmethyl compounds which can be cleaved by irradiation. Similar compositions are for example described in EP 445624.

Further customary additives (G), depending on the intended use, are optical brighteners, wetting agents or leveling assistants.

In order to cure thick and pigmented coatings it is appropriate to add glass microspheres or pulverized glass fibres, as described for example in U.S. Pat. No. 5,013,768.

The choice of additive(s) (G) is made depending on the field of application and on properties required for this field. The additives described above are customary in the art and accordingly are added in amounts which are usual in the respective application.

In certain cases it may be of advantage to use mixtures with known photoinitiators (B1), for example mixtures with camphor quinone, benzophenone, benzophenone derivatives, acetophenone, acetophenone derivatives, for example α-hydroxycycloalkyl phenyl ketones or 2-hydroxy-2-methyl-1-phenyl-propanone, dialkoxyacetophenones, α-hydroxy- or α-aminoacetophenones, e.g. (4-methylthiobenzoyl)-1-methyl-1-morpholinoethane, 4-aroyl-1,3-dioxolanes, benzoin alkyl ethers and benzil ketals, e.g. dimethyl benzil ketal, phenylglyoxalic esters and derivatives thereof, dimeric phenylglyoxalic esters, diacetyl, peresters, e.g. benzophenone tetracarboxylic peresters as described for example in EP 126541, monoacyl phosphine oxides, e.g. (2,4,6-trimethyl-benzoyl)diphenylphosphine oxide, bisacylphosphine oxides, bis(2,6-dimethoxy-benzoyl)-(2,4,4-trimethyl-pentyl)phosphine oxide, bis(2,4,6-trimethylbenzoyl)phenylphosphine oxide, bis(2,4,6-trimethylbenzoyl)-2,4-dipentoxyphenylphosphine oxide, trisacylphosphine oxides, oxime esters, e.g. 1-phenyl-1,2-propanedione-2-O-benzoyl oxime, 1-phenyl-1,2-propanedione-2-O-ethoxycarbonyl oxime, halomethyltriazines, e.g. 2-[2-(4-methoxy-phenyl)-vinyl]-4,6-bis-trichloromethyl-[1,3,5]triazine, 2-(4-methoxy-phenyl)-4,6-bis-trichloromethyl-[1,3,5]triazine, 2-(3,4-dimethoxy-phenyl)-4,6-bis-trichloromethyl-[1,3,5]triazine, 2-methyl-4,6-bis-trichloromethyl-[1,3,5]triazine, 2-(4-N,N-di(ethoxycarbonylmethyl)aminophenyl)-4,6-bis-trichloromethyl-[1,3,5]triazine, 2-(4-methoxy-naphthyl)-4,6-bis-trichloromethyl-[1,3,5]triazine, 2-(1,3-benzodioxol-5-yl)-4,6-bis-trichloromethyl-[1,3,5]triazine, 2-[2-[4-(pentyloxy)phenyl]ethenyl]-4,6-bis-trichloromethyl-[1,3,5]triazine, 2-[2-(3-methyl-2-furanyl)-ethenyl]-4,6-bis-trichloromethyl-[1,3,5]triazine, 2-[2-(5-methyl-2-furanyl)-ethenyl]-4,6-bis-trichloromethyl-[1,3,5]triazine, 2-[2-(2,4-dimethoxy-phenyl)-ethenyl]-4,6-bis-trichloromethyl-[1,3,5]triazine, 2-[2-(2-methoxy-phenyl)ethenyl]-4,6-bis-trichloromethyl-[1,3,5]triazine, 2-[2-[4-isopropyloxyphenyl]-ethenyl]-4,6-bis-trichloromethyl-[1,3,5]triazine, 2-[2-(3-chloro-4-methoxy-phenyl)ethenyl]-4,6-bis-trichloromethyl-[1,3,5]triazine, 2-[2-bromo-4-N,N-di(ethoxycarbonylmethyl)amino-phenyl]-4,6-bis-trichloromethyl-[1,3,5] triazine, 2-[2-chloro-4-N,N-di(ethoxycarbonylmethyl)amino-phenyl]-4,6-bis-trichloromethyl-[1,3,5]triazine, 2-[3-bromo-4-N,N-di(ethoxycarbonylmethyl)amino-phenyl]-4,6-bis-trichloromethyl-[1,3,5]triazine, 2-[3-chloro-4-N,N-di(ethoxycarbonylmethyl)amino-phenyl]-4,6-bis-trichloromethyl-[1,3,5]triazine, or other halomethyltriazines as described for example in G. Buhr, R. Dammel and C. Lindley Polym. Mater. Sci. Eng. 61, 269 (1989), and EP 0262788; halomethyl-oxazol photoinitiators, such as described in U.S. Pat. No. 4,371,606 and U.S. Pat. No. 4,371,607; 1,2-disulfones, such as described in E. A. Bartmann, Synthesis 5, 490 (1993); hexaarylbisimidazole, and hexaarylbisimidazole/coinitiators systems, e.g. ortho-chlorohexaphenyl-bisimidazole combined with 2-mercaptobenzthiazole, ferrocenium compounds, or titanocenes, e.g. bis(cyclopentadienyl)-bis(2,6-difluoro-3-pyrrylphenyl)titanium.

Where the novel systems are employed in hybrid systems, use is made, in addition to the free-radical hardeners, of cationic photoinitiators, of peroxide compounds, such as benzoyl peroxide (other suitable peroxides are described in U.S. Pat. No. 4,950,581 column 19, lines 17-25), of aromatic sulfonium-, phosphonium- or iodonium salts as described for example in U.S. Pat. No. 4,950,581, column 18, line 60 to column 19, line 10 or cyclopentadienyl-arene-iron(II) complex salts, for example ($\eta^6$-iso-propylbenzene)($\eta^5$-cyclopentadienyl)iron(II) hexafluorophosphate, as well as oxime sulfonic acid esters, as are, for example described in EP 780729. Also pyridinium and (iso)quinolinium salts as described e.g. in EP 497531 and EP 441232 may be used in combination with the new photoinitiators.

Subject of the invention therefore also is a composition comprising additionally at least one photoinitiator (B1).

The additional photoinitiator as a component (B1) usually is added in an amount of 0.015 to 80 parts by weight, preferably 0.03 to 60 parts by weight, based on 100 parts by weight of component (A).

The invention also pertains to compositions comprising 100 parts by weight of component (A), 0.015 to 100 parts by weight of component (B), 5 to 200 parts by weight of component (C) and 0.015 to 80 parts by weight of component (E).

The composition is applied uniformly to a substrate by means of known coating techniques, for example by spin coating, dip coating, knife coating, curtain coating, screen coating, brushing, spraying, especially by electrostatic spraying, and reverse-roll coating, and also by means of electrophoretic deposition. It is also possible to apply the photosensitive layer to a temporary, flexible support and then to coat the final substrate, for example a copper-clad circuit board, by transferring the layer via lamination.

The quantity applied (coat thickness) and the nature of the substrate (layer support) are dependent on the desired field of application. The range of coat thicknesses generally comprises values from about 0.1 μm to more than 10 mm, for example 0.1 μm to 1 mm, preferably 0.3 μm to 200 μm.

Following the coating of the substrates, the solvent is removed, generally by drying, to leave a coat of the photoresist on the substrate.

The term "imagewise" exposure includes both, exposure through a photomask comprising a predetermined pattern, for example a slide, a chromium mask, a stencil mask or a reticle, as well as exposure by means of a laser or light beam, which for example is moved under computer control over the surface of the coated substrate and in this way produces an image. The computer-controlled irradiation could also be achieved by electron beams. It is also possible to use masks made of liquid crystals that can be addressed pixel by pixel to generate digital images, as is, for example, described by A. Bertsch, J. Y. Jezequel, J. C. Andre in Journal of Photochemistry and Photobiology A: Chemistry 1997, 107, p. 275-281 and by K.P. Nicolay in Offset Printing 1997, 6, p. 34-37.

The photosensitivity of the novel compositions can extend in general from about 190 nm to 600 nm (UV-vis region). Suitable radiation is present, for example, in sunlight or light from artificial light sources. Consequently, a large number of very different types of light sources are employed. Both point sources and arrays ("lamp carpets") are suitable. Examples are carbon arc lamps, xenon arc lamps, medium-, high-, super high- and low-pressure mercury lamps, possibly with metal halide dopes (metal-halogen lamps), microwave-stimulated metal vapor lamps, excimer lamps, superactinic fluorescent tubes, fluorescent lamps, argon incandescent lamps, electronic flashlights, photographic flood lamps, light emitting diodes (LED), electron beams and X-rays. The distance between the lamp and the substrate to be exposed in accordance with the invention may vary depending on the intended application and the type and output of lamp, and may be, for example, from 2 cm to 150 cm. Laser light sources, for example excimer lasers, such as krypton F lasers for exposure at 248 nm are also suitable. Lasers in the visible region can also be employed. UV laser exposure systems provided by Etec and Orbotech(DP-100™ DIRECT IMAGING SYSTEM) are suitable for UV laser direct imaging without photomask.

The invention therefore also provides a process for the photopolymerization of compounds containing ethylenically unsaturated double bonds, which comprises irradiating a composition as described above with electromagnetic radiation in the range from 190 to 600 nm.

As already mentioned, the compositions can be developed by aqueous alkalis. Particularly suitable aqueous-alkali developer solutions are aqueous solutions of tetraalkylammonium hydroxides or of alkali metal silicates, phosphates, hydroxides and carbonates. Minor quantities of wetting agents and/or organic solvents may also be added, if desired, to these solutions. Examples of typical organic solvents, which may be added to the developer liquids in small quantities, are cyclohexanone, 2-ethoxyethanol, toluene, acetone and mixtures of such solvents.

The compositions of the invention have a high sensitivity and a good developability and therefore are particularly suitable in aqueous developable photoresist applications. They have additionally a good thermal stability.

The novel radiation-sensitive compositions find application as negative resists, having a very high sensitivity to light and being able to be developed in an aqueous alkali medium without swelling. They are suitable as photoresists for electronics like electroplating resist, etch resist, both liquid and dry films, solder resist, as resists to manufacture color filters for a variety of display applications or to generate structures in the manufacturing process of plasma-display panels and electroluminescence displays, the production of printing plates, such as offset printing plates or screen printing plates, for the production of printing forms for relief printing, planographic printing, photogravure or of screen printing forms, for the production of relief copies, for example for the production of texts in braille, for the production of stamps, for use in chemical milling or as a microresist in the production of integrated circuits. The compositions further may be used as photopatternable dielectric layer or coating, encapsulating material and isolating coating in the production of computer chips, printed boards and other electric or electronic components. The possible layer supports, and the processing conditions of the coating substrates, are just as varied.

Because the photocurable compositions according to the invention have a good developability and sufficiently high sensitivity to UV light, they are particularly suitable for the production of color filters or color mosaic systems, such as described, for example, in EP 320 264. Color filters usually are employed in the manufacturing of LC displays, projection systems and image sensors. The color filters can be used, for example, for display and image scanner in television receivers, video monitors or computers, in flat panel display technology etc.

In a process to form a color filter, the coloring matters, dyes and pigments of red, green and blue colors are added to the light-sensitive resin composition of the present invention to provide a light-sensitive resin composition layer of any color on a transparent substrate, and then it is subjected to exposing through a photomask typically having a color filter pattern from a side of the coating, developing with a suitable alkali developing solution, and according to necessity, heating. This process is repeated to form the image having plural colors.

In the light-sensitive resin composition of the present invention, with a process in which at least one or more picture elements are formed on a transparent substrate and then an exposure is given from a side of the transparent substrate, on which the above picture elements are not formed, the above picture elements can be utilized as a light-shielding mask. In this case, for example, in the case where an overall exposure is given, a position adjustment of a mask gets unnecessary and a concern on a position slippage thereof is removed. And, it is possible to cure all of the part on which the above picture elements are not formed. Further, in this case, it is possible as well to develop and remove a part of the portion on which the above picture elements are not formed by using partially a light-shielding mask.

Since in either case, no gap is formed between the picture elements which are formed formerly and those which are formed later, the composition of the present invention is suitable for, for example, a forming material for a color filter. To be concrete, the coloring matters, dyes and pigments of red, green and blue colors are added to the light-sensitive resin composition of the present invention, and the processes for forming an image are repeated to form the picture elements of red, green and blue colors. Then, the light-sensitive resin composition to which, for example, the black coloring materials, dyes and pigments are added is provided on an overall face. An overall exposure (or a partial exposure via a light-shielding mask) can be provided thereon to form the picture elements of a black color all over the spaces (or all but a partial region of the light-shielding mask) between the picture elements of red, green and blue colors.

In addition to a process in which the light-sensitive resin composition is coated on a substrate and dried, the light-sensitive resin composition of the present invention can be used as well for a layer transfer material. That is, the light-sensitive resin composition is layer-wise provided directly on a temporary support, preferably on a polyethylene terephthalate film, or on a polyethylene terephthalate film on which an oxygen-shielding layer and a peeling layer or the peeling layer and the oxygen-shielding layer are provided. Usually, a removable cover sheet made of a synthetic resin is laminated thereon for a protection in handling. Further, there can be applied as well a layer structure in which an alkali soluble thermoplastic resin layer and an intermediate layer are provided on a temporary support and further a light-sensitive resin composition layer is provided thereon (see, for example JP 5-173320-A).

The above cover sheet is removed in use and the light-sensitive resin composition layer is laminated on a permanent support. Subsequently, peeling is carried out between those layer and a temporary support when an oxygen-shielding layer and a peeling layer are provided, between the peeling layer and the oxygen-shielding layer when the peeling layer and the oxygen-shielding layer are provided, and between the temporary support and the light-sensitive resin composition layer when either the peeling layer or the oxygen-shielding layer is not provided, and the temporary support is removed.

The photosensitive coloring composition is produced by use of any of a variety of means for dispersion such as a three-roll mill, a sand mill, a ball mill, a kneader, and a paint shaker. The composition is in general applied to a substrate by using a coating method such as spray coating, spin coating, roll coating, or screen coating. A light source such as a super high pressure mercury lamp or a metal halide is typically employed for irradiation.

A glass support, metal, ceramics, and a synthetic resin film can be used as a support for a color filter. Glass and a synthetic resin film which is transparent and have an excellent dimension stability is particularly preferred.

The thickness of the light-sensitive resin composition layer for color filter is usually 0.1 to 10 micrometers, in particular 0.3 to 5 micrometers.

A diluted aqueous solution of an alkali substance is used as a developing solution for the light-sensitive resin composition of the present invention, and further a solution prepared by adding a small amount of a water-miscible organic solvent thereto is included as well.

Examples of suitable alkali materials include alkali metal hydroxides (for example, sodium hydroxide and potassium hydroxide), alkali metal carbonates (for example, sodium carbonate and potassium carbonate), alkali metal bicarbonates (for example, sodium bicarbonate and potassium bicarbonate), alkali metal silicates (for example, sodium silicate and potassium silicate), alkali metal metasilicates (for example, sodium metasilicate and potassium metasilicate), triethanolamine, diethanolamine, monoethanolamine, morpholine, tetraalkylammonium hydroxides (for example, tetramethylammonium hydroxide), or trisodium phosphate. The concetration of the alkali substance is 0.01 to 30 weight %, and pH is preferably 8 to 14.

Suitable organic solvents which are miscible with water include methanol, ethanol, 2-propanol, 1-propanol, butanol, diacetonealcohol, ethylene glycol monomethyl ether, ethylene glycol monoethyl ether, ethylene glycol mono-n-buthyl ether, benzyl alcohol, acetone, methyl ethyl ketone, cyclohexanone, epsilon-caprolactone, gamma-butylolactone, dimethylformamide, dimethylacetoamide, hexamethylphosphoramide, ethyl lactate, methyl lactate, epsilon-caprolactam, and N-methyl-pyrrolidone. The concentration of the organic solvent which is miscible with water is 0.1 to 30 weight %.

Further, a state of the art surface active agent known to the person skilled in the art can be added. The concentration of the surface active agent is preferably 0.001 to 10 weight %.

The developing solution can be used in either form of a bath solution or a spraying solution. In order to remove the non-cured portion of the light-sensitive resin composition layer, there can be combined the methods such as rubbing with a rotary brush and rubbing with a wet sponge. Usually, the temperature of the developing solution is preferably at and around room temperature to 40° C. The developing time is changeable according to the specific kind of the light-sensitive resin composition, the alkalinity and temperature of the developing solution, and the kind and concentration of the organic solvent in the case where it is added. Usually, it is 10 seconds to 3 minutes. It is possible to put a rinsing step after the development processing.

A final heat treatment is preferably carried out after the development processing. Accordingly, a support having a layer which is photopolymerized by exposing (hereinafter referred to as a photocured layer) is heated in an electric furnace and a drier, or the photocured layer is irradiated with an infrared lamp or heated on a hot plate. The heating temperature and time depend on the composition used and the thickness of the formed layer. In general, heating is preferably applied at about 120° C. to about 260° C., for about 5 to about 60 minutes.

The pigment which can be comprised in the composition according to the present invention, including a pigmented color filter resist composition, is preferably a processed pigment, for example a powdery or pasty product prepared by finely dispersing a pigment into at least one resin selected from the group consisting of acrylic resin, vinyl chloride-vinyl acetate copolymer, maleic acid resin and ethyl cellulose resin.

The red pigment comprises, for example, an anthraquinone type pigment alone, a perylene type pigment alone, or a mixture consisting of at least one of them and a disazo type yellow pigment or an isoindoline type yellow pigment, in particular C. I. Pigment Red 177 alone, C. I. Pigment Red 155 alone or a mixture consisting of at least one member of C. I. Pigment Red 177, C. I. Pigment Red 155 and C. I. Pigment Yellow 83 or C. I. Pigment Yellow 139 ("C.I." refers to the Color Index, known to the person skilled in the art and publicly available). Further suitable examples for the pigment are C.I. Pigment Red 105, 144, 149, 176, 177, 185, 202, 209, 214, 222, 242, 254, 255, 264, 272 and C.I. Pigment Yellow 24, 31, 53, 83, 93, 95, 109, 110, 128, 129, 138, 139, 166 and C.I. Pigment Orange 43.

The green pigment comprises for instance a halogenated phthalocyanine type pigment alone or its mixture with a disazo type yellow pigment or an isoindoline type yellow pigment, in particular C. I. Pigment Green 7 alone, C. I. Pigment Green 36 alone, C. I. Pigment Green 37 alone or a mixture consisting of at least one member of C. I. Pigment Green 7, C. I. Pigment Green 36, C. I. Pigment Green 37, C.I. Pigment Green 136 and C. I. Pigment Yellow 83 or C. I. Pigment Yellow 139. Other suitable green pigments are C.I. Pigment Green 15 and 25.

Examples for suitable blue pigments are phthalocyanine type pigments, used either alone or in combination with an dioxazine type violet pigment, for instance, a combination of C. I. Pigment Blue 15:3 and C. I. Pigment Violet 23. Further examples for blue pigments are such of C.I. Blue 15:3, 15:4, 15:6, 16 and 60, i.e. Phthalocyanine CI Pigment Blue 15:3, or Phthalocyanine C.I. Pigment Blue 15:6. Other suitable pigments are such of C.I. Pigment Blue 22, 28, C.I. Pigment Violet 14, 19, 23, 29, 32, 37, 177 and C.I. Orange 73.

The pigment of the black matrix photopolymeric composition preferably comprises at least one member selected from the group consisting of carbon black, titanium black and iron oxide. However, a mixture of other pigments which, in total, give the black appearance, can also be used. For example, also C.I. Pigment Black 1 and 7 can be used alone or in combination.

For any color, combinations of more than two pigments can also be used. Especially suitable in color filter applications are powdery processed pigments prepared by finely dispersing the above mentioned pigments into a resin.

The concentration of the pigment in the total solid component is for example in the range of 5% to 80% by weight, in particular in the range of 10% to 50% by weight.

The pigments in the color filter resist composition have preferably a mean particle diameter smaller than the wavelength of visible light (400 nm to 700 nm). Particularly preferred is a mean pigment diameter of <100 nm.

If necessary, the pigments may be stabilized in the photosensitive composition by pretreatment of the pigments with a dispersant to improve the dispersion stability of the pigment in the liquid formulation.

Examples of the dispersants are commercially available compounds, for example described in JP 10-90891 such as EFKA-46, EFKA-47, S 3000, S 5000, S 22000, and S 24000.

Preferably, the color filter resist composition according to the present invention contains additionally at least one addition polymerizable monomeric compound.

For example, the following compounds can be used singly or in combination with the other monomers as the addition-polymerizable monomer having an ethylenically unsaturated double bond used in the present invention. Specifically, they include t-butyl(meth)acrylate, ethylene glycol di(meth)acrylate, 2-hydroxypropyl(meth)acrylate, triethylene glycol di(meth)acrylate, trimethylolpropane tri(meth)acrylate, 2-ethyl-2-butylpropanediol di(meth)acrylate, pentaerythritol tri(meth)acrylate, pentaerythritol tetra(meth)acrylate, dipentaerythritol hexa(meth)acrylate, dipentaerythritol penta(m- eth)acrylate, polyoxyethylated trimethylolpropane tri(meth) acrylate, tris(2-(meth)acryloyloxyethyl)isocyanurate, 1,4-diisopropenyl-benzene, 1,4-dihydroxybenzene (meth) acrylate, decamethylene glycol di(meth)acrylate, styrene, diallyl fumarate, triallyl trimellitate, lauryl(meth)acrylate, (meth)acrylamide, and xylenebis(meth)acrylamide. Further, there can be used a reaction product of a compound having a hydroxyl group, such as 2-hydroxyethyl(meth)acrylate, 2-hydroxypropyl(meth)acrylate, and polyethylene glycol mono(meth)acrylate with diisocyanate such as hexamethylenediisocyanate, toluenediisocyanate, and xylenediisocyanate. Particularly preferred are pentaerythritol tetraacrylate, dipentaerythritol hexaacrylate, dipenta-erythritol pentaacrylate, and tris(2-acyloyloxyethyl)-isocyanurate.

In a color filter resist composition the whole amount of the monomers contained in the photopolymerizable composition is preferably 5 to 80% by weight, in particular 10 to 70% by weight based on the whole solid components of the composition.

As the binder used in the color filter resist composition, which is soluble in an alkali aqueous solution and insoluble in water, for example, a homopolymer of a polymerizable compound having one or more acid groups and one or more polymerizable unsaturated bonds in the molecule, or a copolymer of two or more kinds thereof, and a copolymer of one or more polymerizable compounds having one or more unsaturated bonds copolymerizable with these compounds and containing no acid group, can be used. Such compounds can be obtained by copolymerizing one or more kinds of a low molecular compound having one or more acid groups and one or more polymerizable unsaturated bonds in the molecule with one or more polymerizable compounds having one or more unsaturated bonds copolymerizable with these compounds and containing no acid group. Examples of acids groups are, a —COOH group, a —SO$_3$H group, a —SO$_2$NHCO— group, a phenolic hydroxy group, a —SO$_2$NH— group, and a —CO—NH—CO— group. Among those, a high molecular compound having a —COOH group is particularly preferred.

Examples of polymerizable compounds having one or more acid group and one or more polymerizable unsaturated bond in the molecule include inter alia the following compounds: Acrylic acid, methacrylic acid, itaconic acid, crotonic acid, maleic acid, vinylbenzoic acid, and cinnamic acid are examples of the polymerizable compounds having one or more —COOH groups and one or more polymerizable unsaturated bonds in a molecule.

Vinylbenzenesulfonic acid and 2-(meth)acrylamide-2-methylpropanesulfonic acid are examples of the polymerizable compounds having one or more —SO$_3$H groups and one or more polymerizable unsaturated bonds.

N-methylsulfonyl(meth)acrylamide, N-ethylsulfonyl(meth)acrylamide, N-phenylsulfonyl(meth)acrylamide, and N-(p-methylphenylsulfonyl)(meth)acrylamide are examples of the polymerizable compounds having one or more —SO$_2$NHCO— groups and one or more polymerizable unsaturated bonds.

Examples of polymerizable compounds having one or more phenolic hydroxy groups and one or more polymerizable unsaturated bonds in a molecule include hydroxyphenyl (meth)acrylamide, dihydroxyphenyl(meth)acrylamide, hydroxyphenyl-carbonyloxyethyl(meth)acrylate, hydroxyphenyloxyethyl(meth)acrylate, hydroxyphenylthioethyl (meth)acrylate, dihydroxyyphenylcarbonyloxyethyl (meth) acrylate, dihydroxyphenyloxyethyl(meth)acrylate, and dihydroxy-phenylthioethyl (meth)acrylate.

Examples of the polymerizable compound having one or more —SO$_2$NH— groups and one or more polymerizable unsaturated bonds in the molecule include compounds represented by formula (a) or (b):

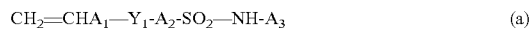

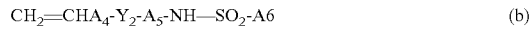

wherein $Y_1$ and $Y_2$ each represents —COO—, —CONA$_7$-, or a single bond; $A_1$ and $A_4$ each represents H or CH$_3$; $A_2$ and $A_5$ each represents $C_1$-$C_{12}$alkylene optionally having a substituent, cycloalkylene, arylene, or aralkylene, or $C_2$-$C_{12}$alkylene into which an ether group and a thioether group are inserted, cycloalkylene, arylene, or aralkylene; $A_3$ and $A_6$ each represents H, $C_1$-$C_{12}$alkyl optionally having a substituent, a cycloalkyl group, an aryl group, or an aralkyl group; and $A_7$ represents H, $C_1$-$C_{12}$alkyl optionally having a substituent, a cycloalkyl group, an aryl group, or an aralkyl group.

The polymerizable compounds having one or more —CO—NH—CO— group and one or more polymerizable unsaturated bond include maleimide and N-acryloyl-acrylamide. These polymerizable compounds become the high molecular compounds comprising a —CO—NH—CO— group, in which a ring is formed together with a primary chain by polymerization. Further, a methacrylic acid derivative and an acrylic acid derivative each having a —CO—NH—CO— group can be used as well. Such methacrylic acid derivatives and the acrylic acid derivatives include, for example, a methacrylamide derivative such as N-acetylmethacrylamide, N-propionylmethacrylamide, N-butanoylmethacrylamide, N-pentanoylmethacrylamide, N-decanoylmethacrylamide, N-dodecanoylmethacrylamide, N-benzoylmethacrylamide, N-(p-methylbenzoyl)methacryl-amide, N-(p-chlorobenzoyl) methacrylamide, N-(naphthyl-carbonyl)methacrylamide, N-(phenylacetyl)-methacryl-amide, and 4-methacryloylaminophthalimide, and an acrylamide derivative having the same substituent as these. These polymerizable compounds polymerize to be compounds having a —CO—NH—CO— group in a side chain.

Examples of polymerizable compounds having one or more polymerizable unsaturated bond and containing no acid group include a compound having a polymerizable unsaturated bond, selected from (meth)acrylates, (meth)acrylamides, an acrylic compound, vinyl ethers, vinyl esters, styrenes, and crotonates, and specifically, include (meth) acrylates such as alkyl (meth)acrylate or substituted alkyl (meth)acrylate (for example, methyl(meth)acrylate, ethyl (meth)acrylate, propyl(meth)acrylate, isopropyl(meth)acrylate, butyl(meth)acrylate, amyl (meth)acrylate, hexyl(meth) acrylate, cyclohexyl(meth)acrylate, ethylhexyl(meth)acrylate, octyl(meth)acrylate, t-octyl(meth)acrylate, chloro-ethyl (meth)acrylate, allyl(meth)acrylate, 2-hydroxy-ethyl(meth) acrylate, 2-hydroxypropyl(meth)acrylate, 4-hydroxybutyl (meth)acrylate, 2,2-dimethyl-3-hydroxy-propyl(meth) acrylate, 5-hydroxypentyl(meth)acrylate, trimethylolpropane mono(meth)acrylate, pentaerythritol mono(meth)acrylate, benzyl (meth)acrylate, methoxy-benzyl(meth)acrylate, chlorobenzyl(meth)acrylate, furfuryl (meth)acrylate, tetrahydrofurfuryl(meth)acrylate, phenoxyethyl(meth)acrylate, and aryl (meth)acrylate (for example, phenyl(meth)acrylate, cresyl(meth)acrylate, and naphthyl (meth)acrylate); (meth)acrylamides such as (meth)acrylamide, N-alkyl(meth)acrylamide (the alkyl group includes, for example, methyl, ethyl, propyl, butyl, t-butyl, heptyl, octyl, ethylhexyl, cyclohexyl, hydroxy-ethyl, and benzyl), N-aryl(meth)acrylamide (the aryl group includes, for example, phenyl, tolyl, nitrophenyl, naphthyl, and hydroxyphenyl), N,N-dialkyl(meth)acryl-amide (the alkyl group includes, for example, methyl, ethyl, butyl, isobutyl, ethylhexyl, and cyclohexyl), N,N-diaryl(meth)acrylamide (the aryl group includes, for example, phenyl), N-methyl-N-phenyl(meth)acryl-amide, N-hydroxyethyl-N-methyl(meth) acrylamide, N-2-acetoamidethyl-N-acetyl(meth)acrylamide, N-(phenyl-sulfonyl)(meth)acrylamide, and N-(p-methylphenyl-sulfonyl)(meth)acrylamide; an allyl compound such as allyl esters (for example, allyl acetate, allyl caproate, allyl caprylate, allyl laurate, allyl palmitate, allyl stearate, allyl benzoate, allyl acetoacetate, and allyl lactate), and allyloxyethanol; vinyl ethers such as alkyl vinyl ether (the alkyl group includes, for example, hexyl, octyl, decyl, ethylhexyl, methoxyethyl, ethoxyethyl, chloroethyl, 1-methyl-2,2-dimethylpropyl, 2-ethylbutyl, hydroxyethyl, hydroxyethoxyethyl, dimethylaminoethyl, diethylamino-ethyl, butylaminoethyl, benzyl, and tetrahydrofurfuryl), and vinyl aryl ether (the aryl group includes, for example, phenyl, tolyl, chlorophenyl, 2,4-dichloro-phenyl, naphthyl, and anthranyl); vinyl esters such as vinyl butylate, vinyl isobutylate, vinyl trimethylacetate, vinyl diethyl-acetate, vinyl barate, vinyl caproate, vinyl chloro-acetate, vinyl dichloroacetate, vinyl methoxyacetate, vinyl butoxyacetate, vinyl phenylacetate, vinyl aceto-acetate, vinyl lactate, vinyl-b-phenylbutylate, vinyl cyclohexylcarboxylate, vinyl benzoate, vinyl salicylate, vinyl chlorobenzoate, vinyl tetrachlorobenzoate, and vinyl naphthoate; styrenes such as styrene, alkylstyrene (for example, methylstyrene, dimethylstyrene, trimethyl-styrene, ethylstyrene, diethylstyrene, isopropylstyrene, butylstyrene, hexylstyrene, cyclohexylstyrene, decyl-styrene, benzylstyrene, chloromethylstyrene, trifluoro-methylstyrene, ethoxymethylstyrene, and acetoxymethyl-styrene), alkoxystyrene (for example, methoxystyrene, 4-methoxy-3-methylstyrene, and dimethoxystyrene), and halogenostyrene (for example, chlorostyrene, dichlorostyrene, trichlorostyrene, tetrachlorostyrene, penta-chlorostyrene, bromostyrene, dibromostyrene, iodostyrene, fluorostyrene, trifluorostyrene, 2-bromo-4-trifluoromethylstyrene, and 4-fluoro-3-trifluoromethylstyrene); crotonates such as alkyl crotonate (for example, butyl crotonate, hexyl crotonate, and glycerine monocrotonate); dialkyl itaconates (for example, dimethyl itaconate, diethyl itaconate, and dibutyl itaconate); dialkyl maleates or fumarates (for example, dimethyl maleate and dibutyl fumarate); and (meth) acrylonitrile.

Hydroxystyrene homo- or co-polymers or a novolak type phenol resin can be used as well, for example, poly(hydroxystyrene) and poly(hydroxystyrene-co-vinylcyclohexanol), a novolak resin, a cresol novolak resin, and a halogenated phenol novolak resin. More specifically, it includes, for example, the methacrylic acid copolymers, the acrylic acid copolymers, the itaconic acid copolymers, the crotonic acid copolymers, the maleic anhydride co-polymers, for example, with styrene as a co-monomer, and maleic acid copolymers, and partially esterified maleic acid copolymers each described in, for example, JP 59-44615-B4 (the term "JP-B4" as used herein means an examined Japanese patent publication), JP 54-34327-B4, JP 58-12577-B4, and JP 54-25957-B4, JP 59-53836-A, JP 59-71048-A, JP 60-159743-A, JP 60-258539-A, JP 1-152449-A, JP 2-199403-A, and JP 2-199404-A, and which copolymers can be further reacted with an amine, as e.g disclosed in U.S. Pat. No. 5,650,263; further, a cellulose derivative having a carboxyl group on a side chain can be used, and particularly preferred are copolymers of benzyl(meth)acrylate and (meth)acrylic acid and copolymers of benzyl (meth)acrylate, (meth)acrylic acid and other monomers, for example as described in U.S. Pat. No. 4,139,391, JP 59-44615-B4, JP 60-159743-A and JP 60-258539-A.

With respect to those having carboxylic acid groups among the above organic binder polymers, it is possible to react some of the carboxylic acid groups with glycidyl(meth)acrylate or an epoxy(meth)acrylate to obtain photopolymerizable organic binder polymers for the purpose of improving the photosensitivity, coating film strength, the coating solvent and chemical resistance and the adhesion to the substrate. Examples are disclosed in, JP 50-34443-B4 and JP 50-34444-B4, U.S. Pat. No. 5,153,095, by T. Kudo et al. in J. Appl. Phys., Vol. 37 (1998), p. 3594-3603, U.S. Pat. Nos. 5,677, 385, and 5,650,233.

Preferably, the organic polymer binder in the color filter resist composition comprises an alkali soluble copolymer comprising, as addition polymerizable monomer units, at least an unsaturated organic acid compound such as acrylic acid, methacrylic acid and the like. It is preferred to use as a further co-monomer for the polymer binder an unsaturated organic acid ester compound such as methyl acrylate, ethyl (meth)acrylate, benzyl(meth)acrylate, styrene and the like to balance properties such as alkali solubility, adhesion rigidity, chemical resistance etc.

The organic polymer binder can either be a random co-polymer or a block-co-polymer, for example, such as described in U.S. Pat. No. 5,368,976.

The weight-average molecular weight of the binders is preferably 500 to 200,000, e.g. 2,000 to 150,000, more preferably 2,000 to 100,000.

These compounds may be used singly or as a mixture of two or more kinds. The content of the binder in the light-sensitive resin composition is preferably 10 to 95 weight %, more preferably 15 to 90 weight % based on the whole solid matters.

Examples for color filter resists, the composition of such resists and the processing conditions are given by T. Kudo et al., Jpn. J. Appl. Phys. Vol. 37 (1998) 3594; T. Kudo et al., J. Photopolym. Sci. Technol. Vol 9 (1996) 109; K. Kobayashi, Solid State Technol. November 1992, p. S15-S18; U.S. Pat. Nos. 5,368,976; 5,800,952; 5,882,843; 5,879,855; 5,866,298; 5,863,678; JP 06-230212-A; EP 320264; JP 09-269410-A; JP 10-221843-A; JP 01-090516-A; JP 10-171119-A, U.S. Pat. Nos. 5,821,016, 5,847,015, 5,882,843, 5,719,008, EP 881541, or EP 902327.

The photoinitiators of the present invention can be used in color filter resists, for example, such as those given as examples above, or can partially or fully replace the known photoinitiators in such resists. It is understood by a person skilled in the art that the use of the photoinitiators of the present invention is not limited to the specific binder resins, crosslinkers and formulations of the color filter resist examples given hereinbefore but can be used in conjunction with any radically polymerizable component in combination with a dye or color pigment or latent pigment to form a photosensitive color filter ink or color filter resist.

The invention also pertains to a color filter comprising a composition according to the invention.

Accordingly, subject of the invention also is a color filter prepared by providing red, green and blue color elements and, optionally a black matrix, all comprising a photosensitive resin and a pigment on a transparent substrate and providing a transparent electrode either on the surface of the substrate or on the surface of the color filter layer, wherein said photosensitive resin comprises a polyfunctional acrylate monomer, an organic polymer binder and a photopolymerization initiator as described above. The monomer and binder components, as well as suitable pigments are as described above. In the manufacture of color filters the transparent electrode layer can either be applied on the surface of the transparent substrate or can be provided on the surface of the red, green and blue picture elements and the black matrix. The transparent substrate is for example a glass substrate which can additionally have an electrode layer on its surface.

It is preferred to apply a black matrix between the color areas of different color in order to improve the contrast of a color filter.

Instead of forming a black matrix using a photosensitive composition and patterning the black photosensitive composition photolithographically by patternwise exposure (i.e. through a suitable mask) to form the black pattern separating the red green and blue colored areas on the transparent substrate it is alternatively possible to use an inorganic black matrix. Such inorganic black matrix can be formed from deposited (i.e. sputtered) metal (i.e. chromium) film on the transparent substrate by a suitable imaging process, for example utilizing photolithographic patterning by means of an etch resist, etching the inorganic layer in the areas not protected by the etch resist and then removing the remaining etch resist.

There are different methods known how and at which step in the color filter manufacturing process the black matrix can be applied. It can either be applied directly on the transparent substrate prior to formation of the red, green and blue color filter as already mentioned above, or it can be applied after the red, green and blue pixels are formed on the substrate.

In a different embodiment of a color filter for a liquid crystal display, according to U.S. Pat. No. 5,626,796, the black matrix can also be applied on the substrate opposite to the RGB color filter element-carrying substrate, which is separated from the former by a liquid crystal layer.

If the transparent electrode layer is deposited after applying the red, green and blue color filter elements and—optionally—the black matrix, an additional overcoat film as protective layer can be applied on the color filter layer prior to deposition of the electrode layer, for example, as described in U.S. Pat. No. 5,650,263.

It is obvious to those skilled in the art, that the photosensitive compositions of the present invention can be used for generating red, green and blue color pixels and a black matrix, for the manufacture of a color filter, regardless of the above described differences in processing, regardless of additional layers which can be applied and regardless of differences in the design of the color filter. The use of a composition according to the present invention to form colored elements shall not be regarded as limited by different designs and manufacturing processes of such color filters.

Further, in the color filter the total solid component of each color may contain an ionic impurity-scavenger, e.g. an organic compound having an epoxy group. The concentration of the ionic impurity scavenger in the total solid component generally is in the range from 0.1% by weight to 10% by weight.

Examples of color filters, especially with respect to the above described combinations of pigments and ionic impurity scavenger are given in EP 320264. It is understood, that the photoinitiators according to the present invention can replace the triazine initiator compounds in the color filter formulations described in EP 320264.

The compositions according to this invention can comprise additionally a crosslinking agent which is activated by an acid, for example as described in JP 10 221843-A, and a compound which generates acid thermally or by actinic radiation and which activates a crosslinking reaction.

The compositions according to this invention can also comprise latent pigments which are transformed into finely dispersed pigments during the heat treatment of the latent pigment containing photosensitive pattern or coating. The heat treatment can be performed after exposure or after development of the latent pigment-containing photoimageable layer. Such latent pigments are soluble pigment precursors which can be transformed into insoluble pigments by means of chemical, thermal, photolytic or radiation induced methods as described, for example, in U.S. Pat. No. 5,879,855. This transformation of such latent pigments can be enhanced by adding a compound which generates acid at actinic exposure or by adding an acidic compound to the composition. Therefore, a color filter resist can also be prepared, which comprises a latent pigment in a composition according to this invention.

The light-sensitive composition of the present invention can suitably be used for forming a color filter but will not be limited to this application.

The photosensitive compositions according to the invention can further be used for manufacturing spacers, which control a cell gap of the liquid crystal part in liquid crystal display panels. Since the properties of light transmitted or reflected through the liquid crystal layer in a liquid crystal display are dependent on the cell gap, the thickness accuracy and uniformity over the pixel array are critical parameters for the performance of the liquid crystal display unit. In a liquid crystal cell, the spacing between the substrates in the cell is maintained constant by sparsely distributing glass or polymer spheres about several micrometers in diameter as spacers between the substrates. The spacers are thus held between the substrates to maintain the distance between the substrates at a constant value. The distance is determined by the diameter of the spacers. The spacers assure the minimum spacing between the substrates; i.e., they prevent a decrease in distance between the substrates. However, they cannot prevent the substrates from being separated apart from each other, i.e., the increase in distance between the substrates. Additionally, this method of using spacer beads has problems of the uniformity in the diameter of spacer beads and difficulty in the even dispersion of spacer beads on the panel, as well as nonuniform orientation and decrease in brightness and/or optical aperture depending on the location of spacers on pixel array region. Liquid crystal displays having a large image display area have recently been attracting much attention. However, the increase in the area of a liquid crystal cell generally produces the distortion of the substrates constituting the cell. The layer structure of the liquid crystal tends to be destroyed due to the deformation of the substrate. Thus, even when spacers are used for maintaining the spacing between the substrates constant, a liquid crystal display having a large image display area is unfeasible because the display experiences disturbances. Instead of the above spacer sphere dispersion method, a method of forming columns in the cell gap as spacers has been proposed. In this method, columns of a resin are formed as spacers in the region between the pixel array region and the counter electrode to form a prescribed cell gap. Photosensitive materials having adhesive properties with photolithography are commonly used, for instance, in the manufacturing process of color filters. This method is advantageous compared with the conventional method using spacer beads in the points that location, number and height of the spacers may be controlled freely. In a color liquid crystal display panel, such spacers are formed in the nonimaging area under black matrix of color filter elements. Therefore, the spacers formed using photosensitive compositions do not decrease brightness and optical aperture.

Photosensitive compositions for producing protective layer with spacers for color filters are disclosed in JP 2000-81701-A and dry film type photoresists for spacer materials are also disclosed in JP 11-174459-A and JP 11-174464-A. As described in the documents, the photosensitive compositions, liquid and dry film photoresists, are comprising at least an alkali or acid soluble binder polymer, a radically polymerizable monomer, and a radical initiator. In some cases, thermally crosslinkable components such as epoxide and carboxylic acid may additionally be included.

The steps to form spacers using a photosensitive composition are as follows:

a photosensitive composition is applied to the substrate, for instance a color filter panel and after the substrate is prebaked, it is exposed to light through a mask. Then, the substrate is developed with a developer and patterned to form the desired spacers. When the composition contains some thermosetting components, usually a postbaking is carried out to thermally cure the composition.

The photocurable compositions according to the invention are suitable for producing spacers for liquid crystal displays (as described above) because of their high sensitivity.

The photosensitive compositions according to the invention are also suitable for manufacturing interlayer insulating layers or dielectric layers in a liquid crystal display, and more particularly in a reflection type liquid crystal display including an active matrix type display having a thin film transistor (TFT) as a switching device, and a passive matrix type without a switching device.

In recent years, liquid crystal displays have, for example, been widely used for pocket-type TV sets and terminal devices for communication by virtue of its small thickness and light weight. A reflection type liquid crystal display without necessity of using a back light is in particular in demand because it is ultra-thin and light-weight, and it can significantly reduce power consumption. However, even if a back light is removed out of a presently available transmission type color liquid crystal display and a light reflection plate is added to a lower surface of the display, it would cause a problem in that the efficiency of utilizing lights is low, and it is not possible to have practical brightness.

As a solution to this problem, there have been suggested various reflection type liquid crystal displays for enhancing an efficiency of utilizing lights. For instance, a certain reflection type liquid crystal display is designed to include a pixel electrode having reflection function.

The reflection type liquid crystal display includes an insulating substrate and an opposing substrate spaced away from the insulating substrate. A space between the substrates is filled with liquid crystals. A gate electrode is formed on the insulating substrate, and both the gate electrode and the insulating substrate are covered with a gate insulating film. A semiconductor layer is then formed on the gate insulating film above the gate electrode. A source electrode and a drain electrode are also formed on the gate insulating film in contact with the semiconductor layer. The source electrode, the drain electrode, the semiconductor layer, and the gate electrode cooperate with one another to thereby constitute a bottom gate type TFT as a switching device.

An interlayer insulating film is formed covering the source electrode, the drain electrode, the semiconductor layer, and the gate insulating film therewith. A contact hole is formed throughout the interlayer insulating film on the drain electrode. A pixel electrode made of aluminum is formed on both the interlayer insulating film and an inner sidewall of the contact hole. The drain electrode of the TFT is eventually in contact with the pixel electrode through the interlayer insulating film. The interlayer insulating layer is generally designed to have a roughened surface by which the pixel electrode acts as a reflection plate which diffuses lights to get a wider angle for viewing (angle of visibility).

The reflection type liquid crystal display remarkably enhances an efficiency of using lights by virtue that the pixel electrode acts as a light reflection plate.

In the above-mentioned reflection type liquid crystal display, the interlayer insulating film is designed to have projections and recesses by photolithography. To form and control a fine shape of the projections and recesses in micrometer order for surface roughness and to form contact holes, photolithography methods using positive and negative photoresists are used. The compositions according to the invention are especially suitable for these resists.

The photosensitive compositions according to the invention are also suitable for manufacturing microlens arrays used in liquid crystal display panels, image sensors and the like.

Microlenses are microscopic passive optical components that fit on active optoelectronic devices such as detectors, displays, and light emitting devices (light-emitting diodes, transversal and vertical cavity lasers) to improve their optical input or output quality. The areas of applications are wide and cover areas such as telecommunications, information technology, audio-visual services, solar cells, detectors, solid-state light sources, and optical interconnects. Present optical systems use a variety of techniques to obtain efficient coupling between microlenses and microoptical devices.

The microlens arrays are used for condensing illuminating light on the picture element regions of a nonluminescent display device, such as a liquid crystal display devices, to increase the brightness of the display, for condensing incident light or as a means for forming an image on the photoelectric conversion regions of a line image sensor used for example in facsimiles and the like to improve the sensitivity of these devices, and for forming an image to be printed on a photosensitive means used in liquid crystal printers or light emitting diode (LED) printers.

The most common application is their use to improve the efficiency of photodetector arrays of a solid-state image sensing device such as a charge coupled device (CCD). In a detector array, the collection of as much light as possible in each detector element or pixel is wanted. If a microlens is put on top of each pixel, the lens collects incoming light and focuses it onto an active area that is smaller than the size of the lens.

According to the prior-art, microlens arrays can be produced by a variety of methods;

(1) A method for obtaining convex lenses wherein a pattern of the lenses in a planar configuration is drawn on a thermoplastic resin by a conventional photolithographic technique or the like, and then the thermoplastic resin is heated to a temperature above the softening point of the resin to have flowability, thereby causing a sag in the pattern edge (so called "reflowing") (see, e.g., JP 60-38989-A, JP 60-165623-A, JP 61-67003-A, and JP 2000-39503-A). In this method, when the thermoplastic resin used is photosensitive, a pattern of the lenses can be obtained by exposure of this resin to light.

(2) A method for forming convex lenses on the basis of a phenomenon in which when a photosensitive resin is exposed to light in a desired pattern by the use of an aligner, unreacted monomers move from the unexposed regions to the exposed regions, resulting in a swell of the exposed regions (see, e.g., Journal of the Research Group in Microoptics Japanese Society of Applied Physics, Colloquium in Optics, Vol. 5, No. 2, pp. 118-123 (1987) and Vol. 6, No. 2, pp. 87-92 (1988)).

On the upper surface of a supporting substrate, a photosensitive resin layer is formed. Thereafter, with the use of a separate shading mask, the upper surface of the photosensitive resin layer is illuminated with light from a mercury lamp or the like, so that the photosensitive resin layer is exposed to the light. As a result, the exposed portions of the photosensitive resin layer swell into the shape of convex lenses to form the light condensing layer having a plurality of microlens.

(3) A method for obtaining convex lenses wherein a photosensitive resin is exposed to light by a proximity exposure technique in which a photomask is not brought into contact with the resin, to cause a blur at the pattern edge, so that the amount of photochemical reaction products is distributed depending upon the degree of blurring at the pattern edge (see, e.g., JP 61-153602-A).

(4) A method for generating a lens effect wherein a photosensitive resin is exposed to light with a particular intensity distribution to form a distribution pattern of refractive index depending upon the light intensity (see, e.g., JP 60-72927-A and JP 60-166946-A).

The photosensitive compositions according to the invention can be used in any one of the above-mentioned methods to form microlens arrays using photocurable resin compositions.

A particular class of techniques concentrates on forming microlenses in thermoplastic resins like photoresist. An example is published by Popovic et al. in the reference SPIE 898, pp. 23-25 (1988). The technique, named reflow technique, comprises the steps of defining the lenses' footprint in a thermoplastic resin, e.g. by photolithography in a photosensitive resin like a photoresist, and subsequently heating this material above its reflow temperature. The surface tension draws the island of photoresist into a spherical cap with a volume equal to the original island before the reflow. This cap is a piano-convex microlens. Advantages of the technique are, amongst others, the simplicity, the reproducibility, and the possibility of integration directly on top of a light-emitting or light-detecting optoelectronic device.

In some cases, an overcoat layer is formed on the patterned lens units with a rectangular shape prior to reflowing to avoid a sagging of the island of the resin in the middle without reflow into a spherical cap in the reflow step. The overcoat acts as a permanent protective layer. The coating layer is also made of a photosensitive composition.

The active energy ray-curable composition used to form the lens section must have a variety of properties, including adhesion to the transparent substrate, and suitable optical characteristics.

Lenses at least with some photoresists in the prior art are not desirable for some applications since the optical transmittance in the blue end of the optical spectrum is poor. Because the photocurable compositions according to the invention have low yellowing properties, both thermally and photochemically, they are suitable for the production of microlens arrays as described above.

The novel radiation-sensitive compositions are also suitable for photo-lithographic steps used in the production process of plasma display panels (PDP), particularly for the imaging forming process of barrier rib, phosphor layer and electrodes.

The PDP is a planar display for displaying images and information by virtue of the emission of light by gas discharge. By the construction of panel and the method of operation, it is known in two types, i.e. DC (direct current) type and AC (alternating current) type.

By way of example, the principle of the DC type color PDP will be briefly explained. In the DC type color PDP, the space intervening between two transparent substrates (generally glass plates) is divided into numerous minute cells by latticed barrier ribs interposed between the transparent substrates. In the individual cells a discharge gas, such as He or Xe, is sealed. On the rear wall of each cell there is a phosphor layer which, on being excited by the ultraviolet light generated by the discharge of the discharge gas, emits visible light of three primary colors. On the inner faces of the two substrates, electrodes are disposed as opposed to each other across the relevant cells. Generally, the cathodes are formed of a film of transparent electroconductive material such as NESA glass. When a high voltage is applied between these electrodes formed on the fore wall and the rear wall, the discharge gas which is sealed in the cells induces plasma discharge and, by virtue of the ultraviolet light radiated consequently, incites the fluorescent elements of red, blue, and green colors to emit lights and effect the display of an image. In the full-color display system, three fluorescent elements severally of the three primary colors of red, blue, and green mentioned above jointly form one picture element.

The cells in the DC type PDP are divided by the component barrier ribs of a lattice, whereas those in the AC type PDP are divided by the barrier ribs which are arranged parallel to each other on the faces of the substrates. In either case, the cells are divided by barrier ribs. These barrier ribs are intended to confine the luminous discharge within a fixed area to preclude false discharge or cross talk between adjacent discharge cells and ensure ideal display.

The compositions according to the invention also find application for the production of one- or more-layered materials for the image recording or image reproduction (copies, reprography), which may be mono- or polychromatic. Furthermore the materials are suitable for color proofing systems. In this technology formulations containing microcapsules can be applied and for the image production the radiation curing can be followed by a thermal treatment. Such systems and technologies and their applications are for example disclosed in U.S. Pat. No. 5,376,459.

The composition of the invention is also suitable for a photopatternable composition for forming a dielectric layer of a multilayer circuit board produced by a sequential build-up process and for producing a solder mask.

The invention therefore also pertains to a photoresist comprising a composition according to the invention.

Accordingly, subject of the invention also is a solder resist comprising a composition as described above.

An image-forming process, e.g. a process for the preparation of solder masks comprises (1) the components of the composition as described above are mixed (2) the resulting composition is applied to the substrate ("coating of the substrate")

(3) the solvent, if present, is evaporated, at elevated temperature, e.g. at a temperature between 80-90° C.

(4) the coated substrate is exposed to electromagnetic radiation through a negative mask (thereby initiating the reaction of the acrylate)

(5) the irradiated sample is developed, by washing with aqueous alkali solution and thereby removing the uncured areas and (6) the sample is thermally cured, e.g. at a temperature about 150° C., thereby initiating the crosslinking between the carboxylic acid and the epoxy component.

This process is another object of the invention.

Another subject of the invention is a process for the photopolymerization of compounds containing ethylenically unsaturated double bonds, which comprises irradiating a composition as described above with electromagnetic radiation in the range from 190 to 600 nm, or with electron beam or with X-rays.

A further subject of the invention is the use of a composition according to the invention for producing pigmented and nonpigmented paints and varnishes, powder coatings, optical fiber coatings, printing inks, printing plates, adhesives, dental compositions, photoresists for electronics like electroplating resists, etch resists, both liquid and dry films, solder resists, as resists to manufacture color filters for a variety of display applications or to generate structures in the manufacturing processes of plasma-display panels, electroluminescence displays and LCD, color filter materials, composite compositions, as composition for encapsulating electrical and electronic components, for producing magnetic recording materials, micromechanical parts, waveguides, optical switches, plating masks, etch masks, colour proofing systems, glass fibre cable coatings, screen printing stencils, for producing three-dimensional objects by means of stereolithography, and as image recording material, especially for holographic recordings, microelectronic circuits, decolorizing materials, decolorizing materials for image recording materials, for image recording materials using microcapsules, as a photoresist material for a UV and visible laser direct imaging system and as a photoresist material used for forming dielectric layers in a sequential build-up layer of a printed circuit board, as well as a process for producing the matters described above.

Another subject of the invention is a coated substrate which is coated on at least one surface with a composition according to the invention and a process for the photographic production of relief images, in which said coated substrate is subjected to imagewise exposure and then the unexposed portions are removed with a developer.

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

The following photoinitiators are used in the examples.

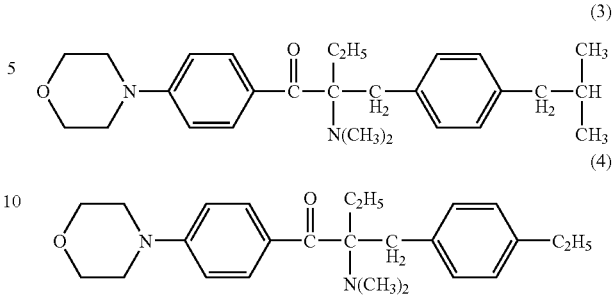

EXAMPLE 1

Preparation of Poly(benzylmethacrylate-co-methacrylic acid)

24 g of benzylmethacrylate, 6 g of methacrylic acid and 0.525 g of azobisisobutyronitrile (AIBN) are dissolved in 90 ml of propylene glycol 1-monomethyl ether 2-acetate (PGMEA). The resulting reaction mixture is placed in a preheated oil bath at 80° C. After stirring for 5 hours at 80° C. under nitrogen, the resulting viscous solution is cooled to room temperature and used without further purification. The solid content is about 25%. The ratio benzylmethacrylate:methacrylic acid is 80:20 by weight.

EXAMPLE 2

Developability Test in a Red Color Resist 160.0 parts by weight of the copolymer of benzylmethacrylate and methacrylic acid according to example 1
40.0 parts by weight of dipentaerythritol hexaacrylate ((DPHA), provided by UCB Chemicals),
40.0 parts by weight of IRGAPHOR RED BT-CF (red pigment, provided by Ciba Specialty Chemicals)
360.0 parts by weight of PGMEA The red color resist dispersion is prepared by mixing the above components and dispersing them by using a Paint conditioner (SKANDEX). To the dispersion, the photoinitiators to be tested are added. The color resists prepared are applied on an aluminum substrate by means of an electric applicator with a wire wound bar. The coated substrates are dried at 80° C. for 10 min. The thickness of the dry film is approximately 2 μm. The resists are developed with 1% sodium carbonate aqueous solution at 30° C. by using a spray type developer (Walter Lemmen, model T21). The development time which is the time to completely remove the resist layer by developing is determined. The lower the value, the better suitable is the formulation. The photoinitiators which are used and the results are collected in table 1.

TABLE 1

Development time of the red color resists

| Photoinitiator | Concentration [parts by weight] | Development Time [sec] |
|---|---|---|
| no | — | 80 |
| (1) | 2.4 | 115 |
| (1) | 6.0 | 115 |
| (2) | 2.4 | 115 |

TABLE 1-continued

Development time of the red color resists

| Photoinitiator | Concentration [parts by weight] | Development Time [sec] |
|---|---|---|
| (2) | 6.0 | 120 |
| (3) | 2.4 | 90 |
| (3) | 6.0 | 90 |
| (4) | 2.4 | 95 |
| (4) | 6.0 | 100 |

EXAMPLE 3

Sensitivity Test

A photocurable formulation is prepared by mixing the following components:

100.0 parts by weight of acrylated acrylcopolymer (ACA200M, provided by Daicel Industries, Ltd., solid content is 50% by weight)

7.5 parts by weight of dipentaerythritol hexaacrylate ((DPHA), provided by UCB Chemicals), 50.0 parts by weight of PGMEA, and photoinitiator to be tested in the amounts as given in table 2

The photoinitiator to be tested is added to the above formulation and mixed. The composition is applied to an aluminum plate using an electric applicator with a wire wound bar. The solvent is removed by heating at 80° C. for 15 min in a convection oven. The thickness of the dry film is approximately 5 μm. To this coating an acetate film is applied, over which a standardized test negative with 21 steps of different optical density (Stouffer step wedge) is placed. The sample is covered with a second UV-transparent film and pressed onto a metal plate by means of vacuum. An interference filter is placed on the top to select the wavelength of 405 nm. Exposure is carried out using a 250 W super high pressure mercury lamp (USHIO, USH-250BY) at a distance of 15 cm. The total exposure dose, measured by an optical power meter (ORC UV Light Measure Model UV-M02 with UV-42 detector), on the test negative film is 4000 mJ/cm². After exposure, the exposed film is developed with 1% sodium carbonate aqueous solution for 1 min at 30° C. by using a spray type developer (Walter Lemmen, model T21). The sensitivity of the initiator system used is characterized by indicating the highest number of the step which remained (i.e. polymerized) after developing. The higher the number of steps, the more sensitive is the tested system. The photoinitiators and results of the tests are given in table 2.

TABLE 2

Results of Sensitivity Tests

| Photoinitiator | Concentration [parts by weight] | Number of Steps after exposure of 4000 J/cm² |
|---|---|---|
| (2) | 7.5 | 3 |
| (2) | 11.0 | 5 |
| (2) | 15.0 | 5 |
| (2) | 20.0 | 7 |
| (4) | 7.5 | 3 |
| (4) | 11.0 | 5 |
| (4) | 15.0 | 5 |
| (4) | 20.0 | 6 |

The invention claimed is:

1. A photopolymerization process for producing pigmented or non-pigmented articles which process comprises irradiating with electromagnetic radiation in the range from 190 to 600 nm, or with electron beam or with X-rays a photosensitive composition comprising, (A) an oligomer or polymer containing at least one carboxylic acid group in the molecule and having a molecular weight of 200,000 or less selected from the group consisting of copolymers of (meth)acrylic acid with ethylenically unsaturated compounds, resins obtained by the reaction of a saturated or unsaturated polybasic acid anhydride with a product of the reaction of an epoxy compound and an unsaturated monocarboxylic acid, and polymers which are an addition product of a carboxyl group-containing resin and an unsaturated compound having an α,β-unsaturated double bond and an epoxy group, (B) at least one photoinitiator compound of formula I

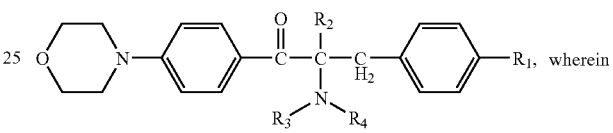

$R_1$ is linear or branched $C_1$-$C_{12}$alkyl;
$R_2$ is linear or branched $C_1$-$C_4$alkyl;
$R_3$ and $R_4$ independently of one another are linear or branched $C_1$-$C_8$alkyl; and (C) an ester of a polyol, wherein the polyol is partially or fully esterified with an ethylenically unsaturated carboxylic acid.

2. A process according to claim 1, wherein in the photosensitive composition $R_1$ is linear or branched $C_1$-$C_4$alkyl,
$R_2$ is methyl, ethyl or propyl and
$R_3$ and $R_4$ independently of one another are linear or branched $C_1$-$C_4$alkyl.

3. A process according to claim 1, wherein the compound of formula I is

1-[4-morpholinophenyl]-2-dimethylamino-2-(4-methylbenzyl)-butane-1-one,

1-[4-morpholinophenyl]-2-dimethylamino-2-(4-ethylbenzyl)-butane-1-one,

1-[4-morpholinophenyl]-2-dimethylamino-2-(4-isopropylbenzyl)-butane-1-one,

1-[4-morpholinophenyl]-2-dimethylamino-2-(4-n-propylbenzyl)-butane-1-one,

1-[4-morpholinophenyl]-2-dimethylamino-2-[4-(2-methylprop-1-yl)-benzyl]-butane-1-one, or 1-[4-morpholinophenyl]-2-dimethylamino-2-(4-n-butylbenzyl)-butane-1-one.

4. A process according to claim 1, wherein component (A) in the photosensitive composition has a molecular weight of 2,000-150,000.

5. A process according to claim 1, wherein the photosensitive composition comprises in addition to the components (A), (B) and (C), at least one benzophenone, thioxanthone, anthraquinone or coumarin photosensitizer compound (E).

6. A process according to claim 1, wherein the photosensitive composition comprises in addition to the components (A), (B) and (C), at least one compound having epoxy groups as thermosetting component (F) and one epoxy curing promoter (G2).

7. A process according to claim 1, wherein the photosensitive composition comprises in addition to the components (A), (B) and (C), at least one ultraviolet-absorber or light stabilizer compound (G3).

8. A process according to claim 1, wherein the photosensitive composition comprises further additives (G), which are selected from the group consisting of colorants, dispersants, thermal polymerization inhibitors, thickeners, antifoaming agents, leveling agents and inorganic fillers.

9. A process according to claim 1, wherein the photosensitive composition comprises 0.015 to 100 parts by weight, based on 100 parts by weight of component (A), of the photoinitiator (B).

10. A process for producing a pigmented or non-pigmented article which process comprises irradiating a coated substrate which is coated on at least one surface with the photosensitive composition according to claim 1.

11. A process according to claim 10 for the photographic production of relief images, wherein the coated substrate is subjected to imagewise exposure and then the unexposed portions are removed with a developer.

12. A process according to claim 10, wherein the pigmented or non-pigmented article is a photoresist.

13. A process according to claim 10, wherein the pigmented or non-pigmented article is a color filter resist.

14. A process for producing a color filter, wherein red, green and blue picture elements and a black matrix are prepared by irradiating, according to claim 1, photosensitive compositions on a transparent substrate and providing a transparent electrode either on the surface of the substrate or on the surface of the color filter layer, wherein said photosensitive compositions comprise, in addition to components (A), (B) and (C), a pigment.

15. A color filter comprising red, green and blue picture elements and a black matrix wherein each picture element and the black matrix comprise an irradiated photosensitive composition of claim 1.

* * * * *